United States Patent [19]

Herrmann et al.

[11] Patent Number: 5,057,618

[45] Date of Patent: Oct. 15, 1991

[54] COMPLEX COMPOUNDS CONTAINING SULFONATED PHENYL PHOSPHANES

[75] Inventors: Wolfgang A. Herrmann; Jurgen Kulpe, both of Freising; Jürgen Kellner, Unterschleissheim; Herbert Riepl, Dachau, all of Fed. Rep. of Germany

[73] Assignee: Hoechst Aktiengesellschaft, Tokyo, Japan

[21] Appl. No.: 444,556

[22] Filed: Nov. 30, 1989

[30] Foreign Application Priority Data

Dec. 2, 1988 [DE] Fed. Rep. of Germany ....... 3840600
Jun. 29, 1989 [DE] Fed. Rep. of Germany ....... 3921295

[51] Int. Cl.$^5$ .................... C07F 9/04; C07F 1/00; C07F 15/00; C07F 13/00
[52] U.S. Cl. .................... 556/21; 556/13; 556/16; 556/19; 556/20; 556/45; 556/110; 556/136; 556/138
[58] Field of Search ............ 556/1, 13, 16, 19, 20, 556/21, 45, 110, 136, 138

[56] References Cited

U.S. PATENT DOCUMENTS

| | | | |
|---|---|---|---|
| 4,336,148 | 6/1982 | Wirth et al. | 556/45 X |
| 4,442,290 | 4/1984 | Hill et al. | 556/21 X |
| 4,625,069 | 11/1986 | Sieole et al. | 556/21 X |
| 4,822,915 | 4/1989 | Murray | 556/21 X |
| 4,857,235 | 8/1989 | Heggie et al. | 556/21 X |

Primary Examiner—Arthur C. Prescott
Attorney, Agent, or Firm—Jordan B. Bierman

[57] ABSTRACT

New complexes of the elements of Groups VIIA, VIIIA, and IB of the Periodic Table* with the trisodium salt of tris(m-sulfophenyl)phosphane as a complex ligand. The complexes are used as catalysts for hydrogenations for the water gas reactions, hydrocarbonyls, hydroformylations, oxidations, carbon-carbon cross-linking reactions (e.g. allene/alkine coupling), and additions of secondary amines to carbon-carbon double bonds.

*according to the IUPAC version.

7 Claims, No Drawings

COMPLEX COMPOUNDS CONTAINING SULFONATED PHENYL PHOSPHANES

The invention relates to a new complex compounds of elements of the Groups IB, VIIA, AND VIIIA of the Periodic Table.* The common feature of these compounds is that they contain the trisodium salt of tris(m-sulfophenyl)phosphane as the complex ligant and optionally other ligands. The compounds are soluble in water without decomposition.

*according to the IUPAC version

BACKGROUND OF THE INVENTION

Complex compounds which contain the trisodium salt of m-trisulfonated triphenylphosphane of the chemical formula $P(C_6H_4-m-SO_3Na)_3$ as the only ligand or as one of several ligands, are little know. DE 27 00 904 C2, Example 12, describes the reaction of bis (1,5-cyclooctadiene)nickel with the trisodium salt of tris(m-sulfophenyl)phosphane (hereinafter TPPTS). A red compound is obtained which is recovered as a solid substance from its aqueous solution by evaporation in a vacuum. The Inventors claim that this compound is the tetrakis-tri-sodium salt of tris[m-sulfophenyl)phosphanenickel(O).

In the same publication, there is also general information on the preparation of TPPTS complex compounds of iron and palladium. Water-soluble compounds, or those compounds which dissolve under the reaction conditions, are reacted with aqueous TPPTS solution in the presence of a reducing agent, e.g. Na[BH$_4$], K[BH$_4$], zinc powder, magnesium, or boron hydrides. Neither the preparation process nor the individual compounds are described in further detail through examples or even characterized.

Complex compounds containing TPPTS as a ligand, without the exact composition of these compounds being known, are formed from metal or metal compounds, TPPTS and optionally other ligands in various reactions. Thus, rhodium complexes with TPPTS ligands have recently gained special significance as components of catalyst systems which are used in the hydroformylation of olefins. Compared with other catalysts which are used for the same reaction, they have the advantage of being soluble in water. Therefore, the hydroforylation can be performed in a heterogeneous reaction medium consisting of aqueous and organic phases (two-phase system), with the result that the reaction product can then be separated from the water-soluble catalyst by simple phase separation. Furthermore, this procedure ensures that the valuable noble metal catalyst can be recovered with almost no loss, or recycled to the synthesis stage. Such a process is described, for example, in the DE 26 27 354 B2.

The addition of hydrogen cyanide to unsaturated cyanide compounds can also be performed in the presence of a compound of zero-valent nickel or iron or palladium of reduced valency and an aqueous solution of a sulfonated triphenylphosphane, in particular an aqueous solution of TPPTS, as a catalyst. This procedure is described in the DE 27 00 904 C2 previously cited. Instead of the nickel salt and TPPTS solution, a specially prepared complex compound, to which the composition Ni(TPPTS)$_4$ is ascribed, can also be used as the catalyst.

In spite of the afore-mentioned advantages of using water-soluble TPPTS complex compounds as catalysts, nothing is known about their use in other reactions.

This situation is probably largely due to the fact that, despite intensive efforts, it has so far not been possible to isolate TPPTS-containing, water-soluble complex compounds in pure form and thus to permit their substance characterization by chemical and physical analytical processes.

The problem to be solved by the present invention was, therefore, to prepare TPPTS-containing complex compounds of certain metals, said compounds having a definite reproducible composition.

SUMMARY OF THE PRESENT INVENTION

The invention consists in new complex compounds of the elements of the Groups IB, VIIA, and VIIIA of the Periodic Table*, with the exception of the reaction product of bis(1,5-cyclooctadiene)nickel with the trisodium salt of tris(m-sulfophenyl)phosphane. The compounds are characterized in that they contain the trisodium salt of tris(m-sulfophenyl)phosphane as the complex ligand and optionally other ligands.

*according to the IUPAC version

DETAILED DESCRIPTION OF THE INVENTION

The new compounds can be represented by the general formula.

In this formula, $L^1$ and $L^2$ denote the same or different ligands, which, in addition to TPPTS, can be bound to the central atom in the complex compound. Typical ligands are CO, NO, PF$_3$, H$_2$O, S, halogen, such as Cl, $\pi$-aromatic ligands such as cyclopentadienyl, $\pi$-olefin ligands, such as cyclooctadiene, and $\pi$-acetylene ligands such as diphenylacetylene. M stands for the elements of the groups IB, VIIA, and VIIIA of the Periodic Table* as the central atom, in particular, manganese, iron, nickel, palladium, platinum, copper, silver or gold; w, x, y and z are integers w and x each denoting 0 to 7y, y being 1 to 6 and z being $\leq 4y$.

The new compounds are crystalline, mostly coloured substances. They are soluble in water without decomposition and can be isolated from the aqueous solution as hydrates in the form of powders or crystals. These hydrates contain one molecule of water per sodium ion. At room temperature the majority are stable in air.

The claimed compounds can be prepared via various routes:

by synthesis from simple compounds, i.e. salts of the element which forms the central atom of the complex compound;

by ligand exchange reaction from complex compounds according to

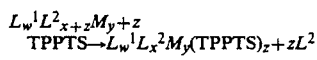

where $L^1$, $L^2$ and M as well as x, y and z have the afore-mentioned meanings with the proviso that z is smaller than or equal to x;

by introduction of TPPTS ligands into complex compounds, said introduction not taking place by simple ligand exchange in the sense of the afore-mentioned equation but by elimination and/or substitution reactions.

For synthesis from simple compounds it is expedient to proceed from water-soluble salts. The type of anion generally has no influence on the course of the reaction. For example, the halides, in particular the chlorides, salts of oxygen acids such as nitrates and sulfates, as well as salts of carboxylic acids such as formates and acetates are all suitable. The salt dissolved in water is reacted with an aqueous TPPTS solution in stoichiometric ratio or in excess. If the oxidation stage of the metal in the complex compound is lower than in the starting salt, either excess TPPTS can act as a reducing agent, or a reducing agent can be added to the reaction solution. Suitable reducing agents are, for example, $Na[BH]_4$ or hydrazine hydrate. In this case it is recommended to conduct the reaction under the exclusion of air as well. In general, the reaction readily takes place at room temperature; only seldom must it be accelerated or completed by increasing the temperature.

When the claimed compounds are prepared by ligand exchange, complex compounds of the respective metals are used as starting substances. Depending on their solubility, they are dissolved in water or in an organic solvent such as aromatic hydrocarbons (e.g. toluene), halogenated hydrocarbons (e.g. chloroform), alcohols (e.g. ethanol), or heterocyclic compounds (e.g. tetrahydrofuran). TPPTS is again used in the form of an aqueous solution and added in stoichiometric ratio or in excess.

With synthesis by ligand exchange it is also sufficient to work at room temperature. Even if the starting complex compound is dissolved in an organic solvent immiscible in water, which means that the reaction takes place in a liquid two-phase system, short reaction times are sufficient; intensive stirring promotes the reaction.

The preparation of the new complex compounds by elimination and substitution reactions takes place in a similar manner and under conditions comparable with those of the synthesis by ligand exchange. Other ligands are introduced into the complex compounds in the known manner, e.g. by feeding in CO or by adding a compound which splits off the nitrosyl radical, a sulfur or hydride group.

In order to work up the reaction product and isolate the new compounds, which are present in aqueous solution regardless of the preparation process used, the water is evaporated in a vacuum, optionally after previous filtration of the solution. In general this route does not lead to pure compounds but contaminated products or also mixtures of various TPPTS complex compounds which have formed concurrently during preparation. It is therefore necessary to use special purification and separating processes to recover the pure substances. Gel chromatography, which is the subject of the German patent application P 38 22 036.9, has proved particularly suitable for solving this task. With this technique attention must also be paid to the exclusion of light or air depending on the properties of the compound in question; the eluent and the elution rate also depend on the particular purification or separation problem in question. After this treatment the compounds are analytically and spectroscopically pure.

As previously mentioned, the new compounds crystallize out of the aqueous solution as hydrates. The anhydrous compounds can be prepared from them without any decomposition occurring by means of water extraction under mild conditions, i.e. at temperatures below the melt or decomposition point and using reduced pressure, preferably a high vacuum. Therefore, the present invention includes both the water-containing and the water-free TPPTS complexes.

The compounds according to the invention are catalytically active and are successfully used as catalysts or components of catalysts in various reactions.

Special mention should be made of the fact that the use of pure compounds prevents side and secondary reactions which reduce the yield and often occur when the catalyst is formed in the reaction mixture "in situ". This situation is due to the fact that the "in situ preparation" is generally connected with the formation of inactive or disturbing by-products. In the cases described by other authors such catalysts still contain without exception free excess TPPTS, which greatly changes the reactivity of the actual TPPTS complex compound. The use of pure TPPTS complex compounds has shown that this class of compound is catalytically active to a much greater degree than was previously known or expected.

Thus the claimed complex compounds are excellent hydrogenation catalysts. For example, they are successfully used for the hydrogenation of olefins to saturated hydrocarbons. In their presence the reaction takes place at normal pressure and temperatures between 20° and 40° C.

The new compounds also cause the water gas equilibrium $$CO + H_2O \rightleftharpoons CO_2 + H_2$$

to shift towards the formation of hydrogen and carbon dioxide. They permit carrying out the reaction at room temperature and a pressure of approximately 1.5 MPa. Hydrogen formed in this manner can, for example, be used for catalytic hydrogenations, e.g. the reaction of organic nitrocompounds to form organic amines. Since with the above-cited reaction carbon monoxide is always present in addition to hydrogen, the gas mixture can also be used for the hydroformylation of olefins.

The preparation of hydrogen from water and carbon monoxide in the presence of the claimed compounds as catalysts also permits the hydrocarbonylation of olefins. Particular mention should be made of the fact that the reaction takes place at relatively low temperatures. Thus, for example, diethylketone is obtained from ethylene at 140° to 150° C. according to the following equation:

$$H_2C=CH_2 + CO + H_2 \rightarrow H_5C_2-CO-C_2H_5$$

Furthermore, the new complex compounds can be used as catalysts for the hydroformylation of olefinically unsaturated compounds. They have proved useful both for the reaction of linear and cyclic olefins and for the reaction of compounds which contain not only a double bond but also functional groups in the molecule.

The oxidation of different classes of compounds is also catalyzed by the new compounds containing TPPTS as a complex ligand. Thus, with iodosylbenzene as an oxidant, the corresponding ketones are obtained from secondary alcohols, epoxides from olefins and diketones from alkines.

The complex compounds according to the invention also catalyze reactions in which new carbon-carbon bonds are formed. An example of this type of reaction is the allene-alkine coupling according to $$R^1R^2C=C=CHX + HC\equiv CR^3 \rightarrow R^1R^2C=C=CH-C\equiv CR^3 + HX$$

where $R^1$, $R^2$ and $R^3$ are alkyl and/or aryl groups, and $R^1$ also hydrogen. An example of this reaction is the reaction of 1-bromoallene with phenylacetylene, which takes place at room temperature under the catalytic influence of the new compounds.

Finally, the claimed complex compounds catalyze the addition of secondary organic amines to carbon-carbon double bonds according to $$R^1R^2C=CH + HNR^3 \rightarrow R^1R^2CH-CH-NR^3$$

The substituents $R^1$, $R^2$ and $R^3$ have the meanings mentioned above.

The following examples describe the preparation and properties of the new compounds.

TPPTS was prepared and purified according to the process described in the DE 32 35 030 Al. OP($C_6H_4$-m-$SO_3Na$)$_3$, referred to as TPPOTS in the following, is separated by means of gel chromatography using the process described in the German patent application P 38 22 036.9. The yields indicated relate to the purified substances.

The following abbreviations were used in the NMR and IR data taken to characterize the new substances:

```
s = singlet, d = doublet, t = triplet
m = multiplet
vw = very weak, w = weak, m = medium,
st = strong, vst = very strong, b = broad band,
sh = shoulder.
```

The Sephadex gels used for chromatographic purification of the new substances are dextranes cross-linked with epichlorohydrin. Fractogel is an oligoethylglycol-glycydyl/methacrylate/pentaerythritol dimethacrylate copolymer.

Example 1: Synthesis of ($\eta^5$-$C_2H_5$)Mn(CO)$_2$(TPPTS)·3 $H_2O$ and ($\eta^5$-$C_5H_5$)Mn(CO)(TPPTS)$_2$·6 $H_2O$ 1.05 g (5 mmol) of ($\eta^5$-$C_5H_5$)Mn(CO)$_3$ ("Cymantren") are dissolved in 70 ml of tetrahydrofuran. The yellow solution is irradiated in a radiation lamp made of duran glass (water-cooled high-pressure mercury lamp TQ 150 manufactured by Original Quarzlampen Gesellschaft mbH, Hanau) for 90 minutes at 15° C. The carmine red solution is then added to a solution of 1.42 g (2.5 mmol) of TPPTS in 10 ml of water. It is stirred for 16 hours, during which the organic phase loses its color and the aqueous phase turns orange. After the phases have separated, the aqueous phase is washed twice, in each case with 25 ml of n-pentane and the water is then evaporated in a vacuum.

The two compounds contained in the residue are separated by column chromatography on Sephadex G-15. The first, yellow-orange zone contains the hydrated di-phosphane complex ($\eta^5$-$C_5H_5$)Mn(CO)(TPPTS)$_2$, the second yellow zone contains the hydrated monophosphane complex ($\eta^5$-$C_5H_5$)Mn(CO)$_2$(TPPTS) in addition to free TPPTS.

Characterization ($\eta^5$-$C_5H_5$)Mn(CO)(TPPTS)$_2$·6 $H_2O$
$^{31}$P-NMR (109.3 MHz, $D_2O$, 5° C.): $\delta = 94.9$ ppm (s).
$^1$H-NMR (270 MHz, $D_2O$, 5° C.): $\delta = 3.97$ ppm s,$C_5H_5$,5H); $= 7.11$–$7.99$ ppm [m,$C_5H_4$, 24H].
IR (cm$^{-1}$, KBr) $v$(CO) = 1828 (st); $v$(SO) = 1221 (sh, vst), 1197 (vst), 1039 (vst), 624 (vst).
Element analysis ($C_{42}H_{41}MnNa_6O_{25}P_2$; 1200.61): Calc. C 36.22; H 2.97; Mn 3.94; O 28.71; P 4.45; S 13.81; Found C 36.15; H 2.68; Mn 3.85; O 27.14; P 4.67; S 14.00.

Characterization ($\eta^5$-$C_5H_5$)Mn(CO)$_2$(TPPTS)·3 $H_2O$
$^{31}$P-NMR (109.3 MHz, $D_2O$, 5° C.): $\delta = 95.7$ (s)
$^1$H-NMR (270 MHz, $D_2O$, 5° C.): $\delta = 4.36$ [s, $C_5H_5$, 5H], $\delta = 7.37$–$8.07$ [m, $C_6H_4$, 12H].
IR (cm$^{-1}$, KBr): $v$(CO) = 1929 (vst), 1852 (vst); $v$(SO) = 1224 (sh, vst), 1199 (vst), 1040 (vst), 622 (vst).

Example 2: Synthesis of Fe(CO)$_3$(TPPTS)$_2$·6 $H_2O$ and Fe(CO)$_4$(TPPTS)·3 $H_2O$ 470 mg (1.3 mmol) of enneacarbonyldiiron, Fe$_2$(CO)$_9$, are boiled with a solution of 587 mg (1.3 mmol) of TPPTS in 50 ml of distilled water for 30 minutes with reflux. An orange-coloured solution forms which is filtered off from the green dodecacarbonyltriiron, Fe$_3$(CO)$_{12}$, which also forms. The filtrate is concentrated to 10 ml and subjected to column chromatography on Sephadex G-15. Five zones form, the first two being collected:

1st fraction: Fe(CO)$_3$(TPPTS)$_2$·6 $H_2O$, yellow solid. Yield 669 mg (38%).
Characterization: $^{31}$P-NMR (109.3 MHz, $D_2O$, +28° C.): $\delta = 74.76$ ppm; IR (cm$^{-1}$, KBr): 1885 vst (vCO).
Element analysis ($C_{39}H_{36}FeNa_6O_2P_2S_6$; 1383.28): Calc. C 31.36; H 2.86; Fe 4.00; P 4.50; Found C 33.80; H 2.80; Fe 3.42; P 4.09.

2nd fraction: Fe(CO)$_4$(TPPTS)·3 $H_3O$, orange solid. Yield: 167 mg (16%).
Characterization: $^{31}$P-NMR (109.3 MHz, $D_2O$, +28° C.): 84.95 ppm; IR (cm$^{-1}$, KBr): 2050 vst, 1977 vst, 1944 vst (vCO).
Element analysis ($C_{22}H_{18}FeNa_3O_{16}PS_3$; 789.49); Calc. C 35.88; H 2.27; P 3.92; Fe 7.06; Found C 34.30; H 2.46; P 4.40; Fe 6.90.

Example 3: Synthesis of Ru(NO)$_2$(TPPTS)$_2$·6 $H_2O$

Variant A. A boiling solution of 1.71 g (3 mmol) of TPPTS in 25 ml of ethanol and 15 ml of water is mixed with 0.13 g (0.5 mmol) of RuCl$_3$·3 $H_2O$ in 10 ml of ethanol. Then a solution of 100 mg (2.6 mmol) of Na[BH$_4$] in 10 ml of ethanol is slowly added dropwise until the solution has turned deep violet (about ⅓ of the solution). Then 210 mg (1.0 mmol) of Diazald ®, (N-methyl-N-nitroso-p-toluene sulfonamide), dissolved in 10 ml of ethanol, and the rest of the sodium boranate solution are added quickly. The mixture is boiled for another 10 minutes with reflux and then cooled to room temperature. A reddish brown precipitate is formed, which is filtered off through a glass sinter, washed with ethanol and purified by column chromatography on Sephadex G-15. From the first grey-black zone a black substance is isolated (5 mg) whose IR spectrum contains not only $v$(SO) vibrations of TPPTS but also bands at 1961 (s) and 1847 (m). The desired ruthenium complex is then recovered from the red zone which follows immediately. Yield: 370 mg (53%); red crystals.

Variant B. 0.13 g (0.5 mmol) of RuCl$_3$·3 $H_2O$ in 10 ml of ethanol, 2 ml of triethylamine and 200 mg of Diazald ® in 10 ml of ethanol are added to a boiling solution of 1.71 g (3 mmol) of TPPTS in 20 ml of ethanol and 10 ml of water. After another 3 ml of triethylamine have been added, the reaction mixture is boiled for another 5 min under reflux. Then it is left to cool to room temperature, filtered through a glass sinter and the solvent is removed from the filtrate in a vacuum. The raw product is purified by column chromatography on Sephadex G-15. Yield: 430 mg (62%); red crystals.

Characterization: $^{31}$P-NMR (109.3 MHz, D$_2$O, 5° C.): δ=56.0 ppm (s). IR (KBr, cm$^{-1}$): ν(SO)=1224 (sh, vst), 1199 (vst), 1040 (vst), 624 (vst); ν(NO)=1675 (st).

Element analysis (C$_{36}$H$_{36}$N$_2$Na$_6$O$_{26}$P$_2$RuS$_6$; 1405.99); Calc. C 30.75; H 2.58; N 1.99; O 29.59; P 4.41; Ru 7.19; S 13.68; Found C 30.56; H 2.76; N 1.68; O 28.84; P 4.11; Ru 7.01; S 14.72;

Example 4: Synthesis of RuCl$_2$(TPPTS)$_2$·6 H$_2$O

Variant A: At room temperature 1.42 g (2.5 mmol) of TPPTS in 15 ml of water are added to 130 mg (0.5 mmol) of ruthenium(III)-chloride-trihydrate, RuCl$_3$·3 H$_2$O, with vigorous stirring, then heated to 50° C. (bath temperature) and left to react at this temperature for 24 hours. Then the water is removed from the clear brown solution in an oil-pump vacuum. The residue is purified by column chromatography on Sephadex G-15. Yield: 430 mg (61%); brown crystals.

Variant B: 570 mg (1 mmol) of TPPTS in 10 ml of water are added to a solution of 120 mg (0.2 mmol) of dichlorotetrakis(triphenylphosphane)ruthenium RuCl$_2$[P(C$_6$H$_5$)$_3$]$_4$ in 20 ml of toluene and the two-phase system formed is stirred for 15 hours at room temperature. After the phases have separated, the organic phase is washed twice, in each case with 5 ml of water. The combined aqueous phases are extracted twice, in each case with 5 ml of toluene. Then the water is removed in an oil-pump vacuum. The raw product is purified by column chromatography on Sephadex G-15. Yield: 160 mg (57%); brown crystals.

Characterization: $^{31}$P-NRM (109.3 MHz, D$_2$O, 5° C.): δ=57.0 ppm (s). IR (KBr, cm$^{-1}$); ν(SO)=1223 (sh, vst), 1198 (vst), 1039 (vst).

Element analysis (C$_{36}$H$_{36}$Cl$_2$Na$_6$O$_{24}$P$_2$RuS$_6$; 1416.89); Calc. C 30.52; H 2.56; P 4.37; S 13.58; Found C 31.12; H 2.84; P 4.21; S 14.04.

Example 5: Synthesis of Co$_2$(CO)$_6$(TPPTS)$_2$·6 H$_2$O 100 mg (0.3 mmol) of octacarbonyl dicobalt, Co$_2$(CO)$_8$, are dissolved in 10 ml of toluene. 400 mg (0.7 mmol) of TPPTS in 10 ml of water are added to the solution and it is stirred for 3 hours at room temperature. After the phases have separated, the organic phase is washed twice, in each case with 5 ml of water, and the combined aqueous phases are washed twice, in each case with 5 ml of toluene. The water is removed in a vacuum and the raw product is purified by column chromatography on Sephadex G-25. Yield: 370 mg (81%); brown powder.

Characterization: $^{31}$P-NMR (109.3 MHz, D$_2$O, 5° C.): δ=68.8 ppm (s); IR (cm$^{-1}$, KBr): ν(CO)=1954 (vst); ν(SO)=1224; (sh, vst), 1200 (vst), 1039 (vst), 623 (vst).

Element analysis (C$_{42}$H$_{36}$Co$_2$Na$_6$P$_2$O$_{30}$S$_6$; 1530.84) Calc. C 32.95; H 2.37; O 31.35; P 4.05; S 12.57; Found C 32.44; H 2.37; O 31.25; P 3.97; S 12.13.

Example 6 Synthesis of CoH(CO)(TPPTS)$_3$·9 H$_2$O

A solution of 120 mg (0.5 mmol) of CoCl$_2$·5 H$_2$O in 5 ml of distilled water is mixed with 1.64 g (3 mmol) of TPPTS and then cooled to 5° C. After the solids have dissolved with stirring, a solution of 32 mg (0.9 mmol) of Na[BH$_4$] in 20 ml of distilled water is added dropwise over a period of 1 hour and at the same time carbon monoxide is introduced. The yellow solution is concentrated in a vacuum to one quarter of its original volume and subjected to column chromatography on Sephadex G-15. The substance shows hardly any sensitivity to air. Yield: 856 mg (89%); canary-yellow powder.

Characterization: $^{31}$P-NMR (109.3 MHz, D$_2$O, 5° C.): δ=45.93 ppm; $^1$H-NMR (270 NH$_3$, D$_2$O, 5° C.): δ=7.32 ppm [m, 27H]; δ=7.29 [br, 9H], δ= −12.35 [q, $^2$J(P,H)=45Hz, 1H]; IR (cm$^{-1}$, KBr): 1953 vst (νCoH), 1904 vst (νCO).

Element analysis (C$_{55}$H$_{55}$CoNa$_9$O$_{37}$P$_3$S$_9$; 1924.99); Calc. C 34.20; H 2.80; Co 3.06; P 4.80; Found C 34.07; H 2.87; Co 3.09; P 4.76.

Example 7: Synthesis of CoH$_2$(TPPTS)$_3$·9 H$_2$O

A solution of 120 mg (0.5 mmol) of CoCl$_2$·5 H$_2$O in 5 ml of distilled water is mixed at 5° C. with 1.64 (3 mmol) of TPPTS. Then a solution of 32 mg (0.9 mmol) of Na[BH$_4$] in 40 ml of distilled water is added dropwise with stirring over a period of 1 hour. The solution is concentrated at 5° C. in a vacuum to about 10 ml and subjected to chromatography on a 15-cm-long Sephadex G-15 column. A high flow rate (approx. 3–4 drops/sec) is chosen and the first part of the red fraction is collected until the zone colour turns green. Over a prolonged period the substance can be stored in its dry state at normal temperature, but in aqueous solution only at around 5° C. Yield: 0.47 g (50%); glass-like, red powder.

Characterization: $^{31}$P-NMR (109.3 MHz, D$_2$O, +28° C.): δ=48.3 ppm (broad); $^1$H-NMR (270 MHz, D$_2$O): (CoH)= −12 ppm (very broad); IR (cm$^{-1}$, KBr): 2008 vst (νCoH).

Example 8: Synthesis of Co$_2$(CO)$_4$(H$_5$C$_6$—C≡C—C$_6$H$_5$)(TPPTS)$_2$·6 H$_2$O 570 mg (1 mmol) of TPPTS in 10 ml of water are added to 250 mg (0.5 mmol) of (μ, η$^2$-diphenylacetylene)hexacarbonyldicobalt in 20 ml of ethanol and left to boil for 15 hours with reflux. After the mixture has cooled to room temperature, the solvent is removed in an oil-pump vacuum, taken up in 10 ml of water, filtered through a sintered disc and the water is removed in an oil-pump vacuum. The blackish brown residue is purified by column chromatography on Sephadex G-15. Yield: 610 mg (74%); blackish brown powder.

Characterization: $^{31}$P-NMR (109.3 MHz, D$_2$O, 5° C.): δ=51.8 ppm (s); IR (KBr, cm$^{-1}$): ν(CO)=2017 (vst), 1960 (vst); ν(SO)=1220 (sh, vst), 1195 (vst), 1039 (vst).

Element analysis: (C$_{54}$H$_{46}$Co$_2$Na$_6$O$_{28}$P$_2$S$_6$; 1653.05); Calc. C 39.24; H 2.80; O 27.10; P 3.75; Found C 39.55 H; 2.67; O 27.16; P 3.68.

Example 9: Synthesis of RhCl(TPPTS)$_3$·9 H$_2$O

Variant A. A solution of 260 mg (1.0 mmol) of RhCl$_3$·3 H$_2$O in 20 ml of water is stirred for about 15 hours after addition of 5.68 g (10 mmol) of TPPTS dissolved in 10 ml of water. The resultant solution, which contains still free phosphane (TPPTS), tris(m-sulfophenyl)phosphane oxide (TPPOTS) as well as small amounts of the binuclear complex [(μ-Cl)Rh(TPPTS)$_2$]$_2$, is purified by column chromatography on Sephadex G-15. Yield: 1.46 g (73%).

Variant B. In a Schlenk tube 100 mg (0.11 mmol) of chlorotris(triphenylphosphane)rhodium(I), ClRh[P(C$_6$H$_5$)$_3$]$_3$, are dissolved in a mixture of 20 ml of toluene and 10 ml of tetrahydrofuran. 20 ml of an aqueous solution of 1.87 g (3.3 mmol) of TPPTS are added to this solution to form a lower layer. After 12 hours of vigorous stirring the aqueous phase of the two-phase system is washed twice, in each case with 5 ml of methylene chloride. The pure compound is obtained by column chromatography on Sephadex G-15. Yield: 180 mg (82%).

Variant C. 100 mg (0.4 mmol) of bis[(μ-chloro){1,2 5,6-$\eta^4$-cyclooctadiene(1.5)}rhodium], [RhCl($\eta^4$-$C_8H_{12}$)]$_2$), are dissolved in 10 ml of methylene chloride. Then 0.68 g (1.2 mmol) of TPPTS in 10 ml of water are added. The two-phase system is stirred intensively for 30 minutes. Then the aqueous phase is isolated and the organic phase extracted twice, in each case with 5 ml of water. The combined aqueous phases are then washed twice, in each case with 5 ml of methylene chloride. The raw product obtained after removal of the solvent is sufficiently pure for most reactions. Depending on the stoichiometry, it can contain small amounts of TPPTS or ($\eta^4$-$C_8H_{12}$)Rh$_2$(μ-Cl)$_2$(TPPTS)$_2$ which can be removed by column chromatography on Sephadex G-15. Yield: 740 mg (93%); red glass-like solid.

Characterization: $^{31}$P-NMR (109.3 MHz, D$_2$O, 5° C.): $\delta$=34.6 ppm (dd); $^1$J(Rh,P$_A$)=144.1 Hz; $\delta$=52.8 ppm (dt) [$^1$J(Rh,P$_B$)=195.8 Hz; IR(cm$^{-1}$, KBr) ν(SO) 1206 (sh, vst), 1181 (vst), 1027 (vst), 741 (vst), 545.(vst), 490 (vst). Calc. C 32.34; H 2.70; P 4.63; Found C 32.30; H 2.71; P 4.60.

Example 10: Synthesis of Rh(NO)(TPPTS)$_3$·9 H$_2$O

Variant A. 0.37 g (0.4 mmol) of Rh(NO)P(C$_6$H$_5$)$_3$]$_3$ are dissolved in 40 ml of toluene. Then 2.27 g (4 mmol) of TPPTS in 20 ml of water are added and the resultant two-phase system is stirred for 24 hours at 25° C. After this time the organic phase has more or less lost its colour. The phases are separated and the organic phase is washed twice, in each case with 5 ml of water. The combined aqueous phases are filtered. Then the water is evaporated in a vacuum. The residue is purified by column chromatography on Sephadex G-25. Yield: 0.58 g (73%); dark-red crystals.

Variant B. 0.26 g (1 mmol) of RhCl$_3$·3 H$_2$O in 20 ml of ethanol, 0.40 g (1.9 mmol) of Diazald ® in 20 ml of ethanol and 0.30 g (7 mmol) of sodium hydroxide in 10 ml of water and 10 ml of ethanol are added in quick succession to a boiling solution of 5.68 g (10 mmol) of TPPTS in a mixture of 40 ml of water and 40 ml of ethanol. The mixture is left to boil for 15 minutes under reflux and cooled to room temperature. After careful neutralisation of the alkaline solution with concentrated sulfuric acid, the water is evaporated in a vacuum. The residue is washed twice, in each case with 10 ml of ethanol. The raw product is purified by column chromatography on Sephadex G-25. Yield: 1.51 g (76%); dark-red crystals.

Variant C. 1.14 g (2 mmol) of TPPTS in 10 ml of water are added to a suspension of 220 mg (0.3 mmol) of Rh(NO)Cl$_2$P(C$_6$H$_5$)$_3$]$_2$ in 15 ml of methylene chloride and the resultant three-phase system is stirred for 20 hours at 25° C. After this time the rhodium complex has completely dissolved and the organic phase has more or less lost its colour. After the phases have separated, the organic phase is washed twice, in each case with 5 ml of water, and the combined aqueous phases are washed twice, in each case with 5 ml of methylene chloride. Then the water is evaporated in a vacuum. The raw product is purified by column chromatography on Sephadex G-25. Yield: 420 mg (70%); dark-red crystals.

Characterization:
$^{31}$P-NMR (109.3 MHz, D$_2$O, 5° C.); $\delta$=48.4 ppm (d); [$^1$J(Rh,P)=176.6 Hz]. IR (cm$^{-1}$; KBr) ν(SO)=1225 (sh, vst), 1200 (vst), 1039 (vst), 623 (vst).

Element analysis (C$_{54}$H$_{54}$Na$_9$NO$_{37}$P$_3$RhS$_9$; 2000.28): Calc. C 32.43; H 2.72; N 0.7; O 29.6; P 4.65; Rh 5.14; S 14.42; Found C 32.61; H 2.68; N 0.60; O 30.90; P 4.54; Rh 5.0; S 14.23.

Example 11: Synthesis of Rh(CH$_3$COO)(TPPTS)$_3$·9 H$_2$O

A solution of 600 mg (1.05 mmol) of TPPTS in 10 ml of water is added to a solution of 100 mg (0.11 mmol) of Rh(CH$_3$COO)[P(C$_6$H$_5$)$_3$]$_3$ in 10 ml of methylene chloride. After 24 hours of stirring, the aqueous phase is isolated and its contents subjected to chromatography on a column packed with Sephadex G-15. Yield: 30 mg (15 red powder.

Characterization: $^{31}$P-NMR (109.3 MHz, D$_2$O, 5° C.): $\delta$=34.5 ppm (dd); [$^1$J(Rh,P$_A$)=144.1 Hz]; $\delta$=53.0 ppm (dt) [$^1$J(Rh,P$_B$)=195.3 Hz; $^2$J(P$_A$,P$_B$)=40.9 Hz].

Element analysis (C$_{56}$H$_{57}$Na$_9$O$_{38}$P$_3$Rh S$_9$: 2029.30): Calc. C 33.15; H 2.83; Na 10.20; Rh 5.07; Found C 33.15; H 2.80; Na 10.00; Rh 5.10.

Example 12: Synthesis of Rh(CO)(OH)(TPPTS)$_2$·6 H$_2$O

Variant A: 100 mg (0.39 mmol) of solid [Rh(CO)$_2$acac] (acac=acetylacetonate) are added to a solution of 2.2 g (3.88 mmol) of TPPTS with vigorous stirring and after 12 hours evaporated to dryness in a vacuum. The residue is taken up in a little water and purified by chromatography on Sephadex G-15. Yield: 310 mg (58%); reddish brown glass.

Variant B: A solution of 250 mg (0.12 mmol) of RhH(CO)-(TPPTS)$_3$·9 H$_2$O in 20 ml of water is heated to boiling for 12 hours with reflux. Then the reaction mixture formed is separated by column chromatography on Sephadex G-15. Yield: 110 mg (63%); reddish brown glass.

Characterization: $^{31}$P-NMR (109.3 MHz, D$_2$O, 21° C.): $\delta$=31,8 ppm (d) [$^1$J(Rh,P)=128.5 Hz); IR (KBr, cm$^{-1}$) ν(CO) 1989, ν(SO) 1196 (sh, st); 1040 (vst) 994 (st), 791 (st), 690 (m).

Element analysis (C$_{37}$H$_{37}$Na$_6$O$_{26}$P$_2$RhS$_6$; 1392.82): Calc. C 31.90 H 2.68 O 29.86 S 13.81 P 4.45 Rh 7.38; 0722 Found C 32.56 H 2.73 O 30.13 S 14.57 P 4.38 Rh 7.21;

Example 13: Synthesis of Rh(CO)Cl(TPPTS)$_2$·6 H$_2$O

Variant A: In a Schlenk tube 1.84 g (1.0 mmol) of RhCl(TPPTS)$_3$·9 H$_2$O are dissolved in 40 ml of nitrogen-saturated water. A red solution is obtained, into which carbon monoxide is introduced over a period of 10 minutes via a gas feed pipe equipped with a sintered disc. The solution becomes much clearer as soon as the carbon monoxide is introduced. After column chromatography of the raw substance on Sephadex G-15 the rhodium complex is obtained in an analytically pure form. Yield: 1.22 g (95%); yellow glass.

Characterization: $^{31}$P-NMR (109.3 MHz, D$_2$O, 5° C.): $\delta$=31.4 ppm (d) [$^1$J(Rh,P)=129.8 Hz]; IR (cm$^{-1}$, KBr): ν(CO 1979 (vst), 1639 (st), ν(SO) 1211 (sh, vst), 1150 (vst), 1041 (vst), 789 (st).

Element analysis (C P2Rh S6; 1411.27): Calc. C 31.49; H 2.57; Cl 2.51; O 28.34; P 4.39; Rh 7.29; S 13.63; Found C 31.50; H 2.70; Cl 2.50; O 29.94; P 4.14; Rh 7.30; S 13.95.

Variant B. 100 mg (0.25 mmol) of tetracarbonylbis(μ-chloro)dirhodium, [(CO)₂RhCl]₂, are dissolved in 10 ml of toluene. 570 mg (1.0 mmol) of TPPTS in 10 ml of water are added and the resultant two-phase system is left to stir for 15 hours at room temperature. After this period the organic phase has lost its colour. The phases are separated and the organic phase is washed twice, in each case with 5 ml of water, the combined aqueous phases are washed twice, in each case with 5 ml of toluene. Then the water is removed in an oil-pump vacuum. The raw product is purified by column chromatography on Sephadex G-15. Yield: 590 mg (84%); yellow powder.

Characterization: $^{31}$P-NMR (109.3 MHz, D₂O, 5° C.): δ=31.3 ppm (d); [$^1$J(Rh,P)=128 Hz]; IR (KBr, cm$^{-1}$): v(CO)=1980 (vst); v(SO)=1224 (sh, vst), 1199 (vst), 1040 (vst).

Element analysis (C₃₇H₃₆O₂₅ClNa₆P₂RhS₆; 1411.27): Calc. C 31.49; H 2.57; Cl 2.51; O 28.34; P 4.39; Rh 7.29; S 13.63; Found C 32.05; H 2.53; Cl 2.64; O 28.26; P 4.14; Rh 7.30; S 13.95.

Example 14: Synthesis of Rh(OH)(TPPTS)₃·9 H₂O

A solution of 260 mg (1.0 mmol) of RhCl₃·3 H₂O in 20 ml of water is stirred for approx. 15 hours after the addition of 5.68 g (10 mmol) of TPPTS dissolved in 10 ml of water. The solution formed containing RhCl(TPPTS)₃, free TPPTS, TPPOTS as well as small amounts of a binuclear complex [Rh(μ-Cl)(TPPTS)₂]₂ is left to stand for at least 24 hours at room temperature and then worked up by column chromatography on Sephadex G-15. After the solvent has been removed, the chlorine-free complex Rh(OH)(H₂O)(TPPTS)₃·9 H₂O is obtained in yields of 70 to 90% as red glass.

Characterization: $^{31}$P-NMR (109.3 MHz, D₂O, 21° C.): δ=35.2 ppm (dd) ; $^1$J(Rh,P$_A$)=143.9 Hz δ=53.48 ppm (dt); $^1$J(Rh,P$_B$)=195.3 Hz; $^2$J(P,P)=40.9 Hz; IR (KBr, cm$^{-1}$) v(SO) 1220 (sh, vst), 1196 (vst), 1038 (vst), 787 (m), 624 (m), 527 (w).

Element analysis (C₅₄H₅₅Na₉O₃₇P₃RhS₉; 1987.25): Calc C 33.63; H 2.79; Cl 0.0; O 29.79; P 4.68; Rh 5.18; S 14.51; Found C 32.59; H 2.89; Cl 0.0; O 30.57; P 4.33; Rh 5.90; S 14.10.

Example 15: Synthesis of [Rh(μ-Cl)(CO)(TPPTS)]₂·6 H₂O 570 mg (1 mmol) of TPPTS in 10 ml of water are added to a solution of 190 mg (0.5 mmol) of bis[(μ-chloro)-dicarbonylrhodium], [Rh(μ-Cl)(CO)₂]₂, in 10 ml of toluene and the two-phase mixture thus formed is stirred for 18 hours at room temperature. After separation of the phases the organic phase is washed twice, in each case with 5 ml of water. The combined aqueous phases are extracted twice, in each case with 5 ml of toluene and filtered. The water is removed from the filtrate in an oil-pump vacuum. Purification takes place by column chromatography on Sephadex G-15. RhCl(CO)(TPPTS)₂·6 H₂O is isolated from the first orange-coloured zone and [Rh(μ-Cl)(CO)(TPPTS)]₂ from the subsequent yellow zone. Yield: 330 mg (42%); yellow powder.

Characterization: $^{31}$P-NMR (109.3 MHz, D₂O, 5° C.): δ=48.2 ppm (d); [$^1$J(Rh,P)=180 Hz]; IR (KBr, cm$^{-1}$) v(CO)=1986 (vst), v(SO)=1224 (sh, vst), 1197 (vst), 1039 (vst).

Element analysis (C₃₈H₃₆Cl₂Na₆O₂₆P₂Rh₂S₆; 1577.65): Calc. C 28.93; H 2.30; O 26.37; P 3.93; Rh 13.05; S 12.19; Found C 29.90; H 2.23; O 27.02; P 3.90; Rh 13.15; S 12.08.

Example 16: Synthesis of Rh₂(TPPTS)₂[P(C₆H₄SO₃Na)₂(C₆H₄-m-SO₃)]₂·10 H₂O 850 mg (1.5 mmol) of TPPTS in 10 ml of water are added to a solution of 100 mg (0.25 mmol) of tetrakis(η²-ethylene)bis(μ-chloro)dirhodium, Rh(μ-Cl)(η²-C₂H₄)₂]₂ in 10 ml of methylene chloride. The two-phase system is stirred for 30 minutes at room temperature, during which the organic phase loses its colour. After separation of the phases the organic phase is extracted twice, in each case with 5 ml of water. The combined aqueous phases are washed twice, in each case with 5 ml of methylene chloride and then filtered. The water is evaporated in an oil-pump vacuum. The raw product is purified by column chromatography on Sephadex G-25. First comes a grey band which is followed by an orange zone from which the rhodium complex compound is isolated. Yield: 320 mg (49%); brownish red powder.

Characterization: $^{31}$P-NMR (109.3 MHz, D₂O, 5° C.): δ=57.8 ppm (d); [$^1$J(Rh,P)=181 Hz]; IR (KBr, cm$^{-1}$) v(SO)=1224 (sh, vst), 1199 (vst), 1139 (vst).

Element analysis (C₇₂H₆₈O₄₆P₄S₁₂Na₁₀Rh₂; 2613.63): Calc. C 33.09; H 2.62; Cl 0.00; O 28.16; P 4.74; Rh 7.87; S 14.72; Found C 33.04; H 2.85; Cl 0.00; O 28.08; P 4.48; Rh 8.00; S 14.16.

Example 17: Synthesis of Rh₂(μ-Cl)₂(η⁴-C₈H₁₂)(TPPTS)₂·6 H₂O

A solution of 454 mg (0.08 mmol) of TPPTS in 10 ml of water is added to a solution of 200 mg (0.4 mmol) of [Rh(μ-Cl)(η⁴-C₈H₁₂)]₂ in 10 ml of methylene chloride. The two-phase system obtained is stirred for 12 hours at room temperature. Then the aqueous phase is isolated, the organic phase is washed twice, in each case with 5 ml of water, and the combined aqueous phases are washed twice, in each case with 5 ml of methylene chloride. In order to remove the residual methylene chloride, the aqueous solution is concentrated to ¾ of its original volume. The resultant solution is subjected to column chromatography on Sephadex G-15. Yield: 510 mg (73%; orange-red powder.

Characterization: $^{31}$P-NMR (109.3 MHz, D₂O, 5° C.): δ=129.0 ppm (d); [$^1$J(Rh,P)=146.2 Hz] $^1$H-NMR (400 MHz, D₂O, 23° C.): δ=2.14 ppm [br s, CH₂, 4H]; δ=2.43 ppm [br s, CH₂, 4H]; δ=4.54 ppm; [CH, 4H); δ=7.28-7.96 [m, C₆H₄, 24 H]; IR (cm$^{-1}$, KBr): 1633 (m), 1399 (st), v(SO 1206 (sh, vst), 1038 (st), 791 (st), 693 (m), 621 (m).

Example 18: Synthesis of Rh₆(CO)₇(TPPTS)₉·27 H₂O 230 mg (0.07 mmol) of Rh₆(CO)₇[P(C₆H₅)₃]₉ are dissolved in 10 ml of chloroform. 1.42 g (2.5 mmol) of TPPTS in 10 ml of water are added with stirring, whereupon the aqueous phase quickly turns yellow. To complete the exchange reaction, the mixture is stirred for another hour and the two phases separated. The organic phase is washed twice, in each case with 5 ml of water. Then the aqueous phases are combined and the water is removed in a vacuum. The residue is purified by column chromatography on Sephadex G-25. Yield: 350 mg (78%); yellowish brown powder.

Characterization: $^{31}$P-NMR (109.3 MHz, D₂O, 5° C.): δ=30.5 ppm [$^1$J(Rh,P)=130 Hz]. Ir (cm$^{-1}$, KBr) v(SO)=1225 (sh, vst), 1200 (vst), 1039 (vst), 623 (vst); v(CO)=1981 (st).

Element analysis ($C_{169}H_{162}Na_{27}O_{115}P_9Rh_6S_{27}$; 6415.61): Calc. C 31.64; H 2.55; O 28.68; P 4.35; S 13.49; Found C 31.96; H 2.93; O 28.83; P 4.29; S 13.69.

Example 19: Synthesis of Ir(NO)(TPPTS)$_3$·9 H$_2$O 850 mg (1.5 mmol) of TPPTS in 10 ml of water are stirred into a solution of 140 mg (0.17 mmol) of dichloronitrosylbis(triphenylphosphane)iridium, IrCl$_2$NO [P(C$_6$H$_5$)$_3$]$_2$ in 30 ml of methylene chloride at room temperature. After only a short time the aqueous phase turns brown whilst the organic phase loses its color. To complete the reaction, the mixture is stirred for another hour and the phases are then separated. The organic phase is washed twice, in each case with 5 ml of water. The combined aqueous phases are extracted twice, in each case with 5 ml of methylene chloride and then the water is evaporated in an oil-pump vacuum. The raw product is purified by column chromatography on Sephadex G-25 or Fractogel TSK HW-40 F. Yield: 160 mg (45%); brown powder.

Characterization: $^{31}$P-NMR (109.3 MHz, D$_2$O, 5° C.): $\delta = 16.7$ ppm (s); Ir (KBr, cm$^{-1}$) v(SO)=1225 (sh, vst), 1198 (vst), 1039 (vst), 623 (st).

Element analysis ($C_{54}H_{54}IrNNa_9O_{37}P_3S_9$; 2089.59): Calc. C 31.04; H 2.60; Cl 0.0; N 0.67; O 28.33; P 4.45; S 13.81; Found C 29.42; H 2.55; Cl 0.0; N 0.61; O 27.90; P 3.90; S 13.41.

Example 20: Synthesis of IrCl(CO)(TPPTS)$_3$·9 H$_2$O 160 mg (0.5 mmol) of Ir(CO)$_3$Cl are suspended in 20 ml of toluene. With vigorous stirring 1.14 g (2 mmol) of TPPTS in 10 ml of water are added at room temperature. After only a short time the aqueous phase turns yellow. To complete the CO substitution, the mixture is stirred for another 24 hours at room temperature and the phases are then separated. The organic phase is washed twice, in each case with 5 ml of water. The combined aqueous phases are extracted twice, in each case with 5 ml of toluene and then filtered. After the solvent has been removed in an oil-pump vacuum, the raw product is purified by column chromatography on Sephadex G-15. Yield: 600 mg (57%); orange-yellow powder.

Characterization: $^{31}$P-NMR (109.3 MHz, D$_2$O, 5° C.): $\delta = -2.8$ ppm (s); IR (KBr, cm$^{-1}$) v(CO)=2005 (m), 1963 (m); v(SO)=1226 (sh, vst), 1200 (vst), 1038 (vst), 623 (vst).

Element analysis ($C_{55}H_{54}ClIrNa_9O_{37}P_3S_9$; 2123.05): Calc. C 31.11; H 2.56; Cl 1.68; Ir 9.05; O 27.88; P 4.38; Found C 30.04; H 2.54; Cl 1.67; Ir 8.76; O 28.13; P 3.99.

Example 21: Synthesis of IrH(CO)(TPPTS)$_3$·9 H$_2$O 290 mg (0.5 mmol) of TPPTS in 10 ml of water are added to 200 mg (0.2 mmol) of carbonylhydridotris(triphenylphosphane)iridium, IrH(CO)P(C$_6$H$_5$)$_3$]$_3$, dissolved in 20 ml of toluene. The resultant two-phase mixture is left to boil for 5 days with reflux. After it has cooled to room temperature, the phases are separated and the organic phase is extracted with 10 ml of water. The combined aqueous phases are washed twice, in each case with 10 ml of toluene and then filtered. The water is evaporated from the filtrate in an oil-pump vacuum. Yield: 310 mg (89%, related to TPPTS); yellow powder.

Characterization: $^{31}$P-NMR (161.9 MHz, D$_2$O, 5° C.): $\delta = 19.2$ ppm (s); $^1$H-NMR (400 MHz, D$_2$O, 5° C.): $\delta = -10.69$ ppm (q, IrH, 1H); [$^2$J(P,H)=20.8 Hz]; $\delta = 7.08$–7.76 ppm (m, C$_6$H$_4$, 12H); IR (KBr, cm$^{-1}$): v(IrH)=2128 (w), v(CO)=1927 (m), v(SO)=1222 (sh, vst), 1196 (vst), 1038 (vst).

Example 23: Synthesis of Ni(TPPTS)$_3$·9 H$_2$O

Variant A. 71 mg (0.3 mmol) of NiCl$_2$l]6 H$_2$O and 0.85 g (1.5 mmol) of TPPTS are dissolved in a mixture of 5 ml of water and 5 ml of ethanol. At $-15°$ C. 34 mg (0.9 mmol) of Na[BH$_4$], dissolved in 5 ml of water and 5 ml of ethanol, are added dropwise over 90 minutes. The reaction solution turns red and then reddish brown. After all the Na[BH$_4$] has been added, the temperature of the solution is allowed to rise to room temperature over a period of 3 hours and the solvent is removed in a vacuum. The raw product is purified by means of column chromatography on Sephadex G-15, the column being cooled to 0° C. Yield: 0.53 g (92%); reddish brown powder.

Characterization: $^{31}$P-NMR (109.3 MHz, D$_2$O/C$_2$H$_5$OH 1:1, $-30°$ C.): $\delta = 22.7$ ppm (s). The chemical shifting of Ni(TPP)$_3$ is $\delta = 23$ ppm [C. A. Tolman, W. C. Seidel and D. H. Gerlach, J. Am. Chem. Soc. 94 (1972) 26691.] IR (KBr, cm$^{-1}$): v(SO)=1222 (sh, vst), 1192 (vst), 1039 (vst), 622 (vst).

Element analysis ($C_{54}H_{54}Na_9NiO_{36}P_6S_9$: 1926.07): Calc. C 33.67; H 2.83; P 4.82; Ni 3.05; P 4.82; Found C 33.74; H 2.87; P 4.69; Ni 3.00; P 4.79.

Variant B. 830 mg (1.45 mmol) of TPPTS in 10 ml of water are stirred vigorously into a solution of 100 mg (0.36 mmol) of bis($\eta^4$-1.5-cyclooctadiene)nickel NI($\eta^4$-C$_8$H$_{12}$)$_2$ in 10 ml of toluene; the aqueous solution rapidly turns reddish brown. To complete the Element analysis ($C_{55}H_{55}IrNa_9O_{37}P_3S_9$; 2088.61): Calc. C 31.63; H 2.65; O 28.34; P 4.45; Found C 31.65; H 2.53; O 28.23; P 4.08.

Example 22: Synthesis of ($\eta^4$-C$_8$H$_{12}$)Ir(Cl)(TPPTS)$_2$·6 H$_2$O 570 mg (1.0 mmol) of TPPTS in 10 ml of water are stirred into a solution of 130 mg (0.2 mmol) of [($\mu$-Cl)Ir($\eta^4$-C$_8$H$_{12}$)]$_2$ in 10 ml of toluene at room temperature. The organic phase loses its colour spontaneously. To complete the reaction, stirring is continued for another 15 minutes. After separation of the phases, the water is evaporated in a vacuum. The raw product is purified by column chromatography on Sephadex G-15. Yield: 770 mg (97%); red crystals.

Characterization: $^{31}$P-NMR (109.3 MHz, D$_2$O, 5° C.): $\delta = 19.0$ ppm (s); $^1$H-NRM (270 MHz, D$_2$O, 5° C.): $\delta = 1.89$ ppm [br, d, 4H, $^2$J(H,H)=7.8 Hz, CH$_2$], $\delta = 2.33$ ppm [br, s, 4H, CH$_2$]; $\delta = 4.32$ ppm [br s, 4H, CH]; $\delta = 7.48$–7.96 ppm [m, 24H, C$_6$H$_4$]; IR (cm$^{-1}$, KBr) v(SO)=1223 (sh, vst), 1199 (vst), 1039 (vst), 623 (vst).

Element analysis ($C_{44}H_{48}ClIrNa_6O_{24}P_2S_6$; 1580.77): Calc. C 33.43; H 3.06; Cl 2.24; O 24.29; P 3.92; S 12.17; Found C 33.56; H 2.99; Cl 2.26; O 23.75; P 3.63; S 12.87.

exchange reaction, the two-phase system is stirred for another 8 hours at room temperature, after which the organic phase has lost its colour. The phases are separated. The organic phase is washed twice, in each case with 5 ml of water, and the combined aqueous phases are extracted twice, in each case with 5 ml of toluene. Then the water is evaporated in a vacuum. The residue is purified by column chromatography on Sephadex G-15 at 0° C. (glass column, l=60 cm, d=1 cm, cooling with Kryomat Julabo F 40, (a circulating cryomat manufactured by Julabo). After a green zone containing decomposition products, there follows a broad, reddish brown zone from which the nickel complex is isolated. Yield: 380 mg (55%); reddish brown powder.

Characterization: $^{31}$P-NMR (109.3 MHz, D$_2$O/C$_2$H$_5$OH 1:1, $-30°$ C.): $\delta=22.7$ ppm (s). The chemical shifting of Ni(TPP)$_3$ is $\delta=23$ ppm [C. A. Tolman, W. C. Seidel and D. H. Gerlach, J. Am. Chem. Soc. 94 (1972) 2669]. IR (KBr, cm$^{-1}$): $\nu$(SO)=1222 (sh, vst), 1192 (vst), 1039 (vst), 622 (vst).

Variant C. 680 mg (1.2 mmol) of TPPTS in 10 ml of water are stirred into a solution of 330 mg (0.3 mmol) of tetrakis(triphenylphosphane)nickel, Ni[P(C$_6$H$_5$)$_3$]$_4$, in 10 ml of toluene at room temperature. The aqueous phase rapidly turns reddish brown. To complete the exchange reaction stirring is continued for another 15 hours and then the phases are separated. The organic phases are washed twice, in each case with 5 ml of water, the combined aqueous phases are extracted twice, in each case with 5 ml of toluene. Then the water is removed in an oil-pump vacuum. The raw product is purified by column chromatography on Sephadex G-15. Yield: 350 mg (61%); reddish brown powder.

Characterization: $^{31}$P-NMR (109.3 MHz, D$_2$O/C$_2$H$_5$OH, $-30°$ C.): $\delta=22.7$ ppm (s) The chemical shifting of Ni(TPP)$_3$ is $\delta=23$ ppm [C. A. Tolman, W. C. Seidel and D. H. Gerlach, J. Am. Chem. Soc. 94 (1972) 2669]. IR (KBr, cm$^{-1}$) $\nu$(SO)=1222 (sh, vst), 1192 (vst), 1039 (vst), 622 (vst).

Element analysis (C$_{54}$H$_{54}$Na$_9$NiO$_{36}$P$_3$S$_9$; 1926.07): Calc. C 33.67; H 2.83; Ni 3.05; P 4.82; O 29.90; Found C 33.74; H 2.87; Ni 3.49; P 4.69; O 30.61.

Example 24: Synthesis of Ni(CO)$_2$(TPPTS)$_2$·6 H$_2$O

Variant A. 170 mg (1 mmol) of Ni(CO)$_4$ are dissolved in 10 ml of toluene and mixed with 2.84 g (5 mmol) of TPPTS, dissolved in 10 ml of water. The resultant two-phase mixture is stirred for 18 hours at 25° C. The aqueous phase is washed with 10 ml of toluene and then the water is removed in a vacuum. The raw product is purified by gel chromatography on Sephadex G-15 (column l=100 cm, d=24 mm). Yield: 0.83 g (61%); yellow powder.

Characterization: $^{31}$-NMR (109.3 MHz, D$_2$O, 5° C.): $\delta=34.9$ ppm (s); IR (cm$^{-1}$, KBr) $\nu$(CO)=1944(st), 2008(st); $\nu$(SO) =1122(sh, vst), 1196(vst), 1040(vst), 624(st).

Element analysis (C$_{38}$H$_{36}$Na$_6$NiP$_2$O$_{26}$S$_6$; 1358.63); Calc. C 33.57; H 2.67; Ni 4.32; O 30.60; P 4.56; Found C 33.52; H 2.52; Ni 4.52; O 29.23; P 4.25.

Variant B. A CO gas stream is passed through a solution of 190 mg (0.1 mmol) of Ni(TPPTS)$_3$·9 H$_2$O in 10 ml of water at room temperature for 15 minutes; the original deep reddish brown solution rapidly turns yellow. Then stirring is continued for another 15 minutes and the solvent is then removed in an oil-pump vacuum. The residue is purified by column chromatography on Sephadex G-15. Yield: 110 mg (81%); yellow powder.

Characterization: $^{31}$P-NMR (109.3 MHz, D$_2$O/C$_2$H$_5$OH 1:1, $-30°$ C.): $\delta=22.7$ ppm (s). The chemical shifting of Ni(TPP)$_3$ is $\delta=23$ ppm C. A. Tolman, W. C. Seidel and D. H. Gerlach, J. Am. Chem. Soc. 94 (1972) 2669]. IR (KBr, cm$^{-1}$) $\nu$(SO)=1222 (sh, vst), 1192 (vst), 1039 (vst), 622 (vst).

Element analysis (C$_{38}$H$_{36}$Na$_6$NiP$_2$O$_{26}$S$_6$; 1358.63): Calc. C 33.57; H 2.67; Ni 4.32; O 30.60; P 4.56; Found C 33.52; H 2.52; Ni 4.52; O 29.23; P 4.25.

Example 25: Synthesis of Ni(PF$_3$)$_2$(TPPTS)$_2$·6 H$_2$O

Variant A. 0.21 g (0.5 mmol) of Ni(PF$_3$)$_4$ are dissolved in 20 ml of tetrahydrofuran. 0.85 g (1.5 mmol) of TPPTS in 10 ml of water are added to the solution and it is heated over a period of 4 hours to boiling point. The aqueous phase has then turned yellow. After cooling to room temperature, the phases are separated and the water phase is washed twice, in each case with 5 ml of toluene, and the solvent is then removed in a vacuum. The raw product is purified by column chromatography on Sephadex G-15. Yield: 0.56 g (76%); yellow powder.

Variant B. 0.13 g (0.3 mmol) of Ni(PF$_3$)$_4$ are dissolved in 10 ml of tetrahydrofuran and 10 ml of toluene. Then 0.51 g (0.9 mmol) of TPPTS in 10 ml of water are added and the resultant two-phase mixture is stirred for 3 hours at 25° C. After this period the aqueous phase has turned yellow. The phases are separated, the aqueous phase is washed twice, in each case with 5 ml of toluene, and evaporated until dry. The raw product is purified by column chromatography on Sephadex G-15. Yield: 0.35 g (78%); yellow powder.

Characterization: $^{31}$P-NMR (109.3 MHz, D$_2$O/EtOH 1:1, $-30°$ C.): $\delta=45.8$ ppm.

Element analysis (C$_{36}$H$_{36}$F$_6$Na$_6$NiO$_{24}$P$_4$S$_6$; 1479.55): Calc. C 29.23; H 2.45; F 7.71; Ni 3.97; O 25.95; P 8.37; S 13.00; Found C 29.10; H 2.50; F 7.60; Ni 3.89; O 26.15; P 8.50; S 13.50.

Example 26: Synthesis of Pd(TPPTS)$_3$·9 H$_2$O

Variant A. 2.27 g (4 mmol) of TPPTS in 20 ml of water are added to a solution of 0.46 g (0.4 mmol) of tetrakis(triphenylphosphane)palladium, Pd[P(C$_6$H$_5$)$_3$]$_4$, in 40 ml of toluene at 25° C. The organic phase rapidly loses its colour. To complete the reaction, stirring is continued for another 15 minutes. Then the phases are separated and the toluene phase is washed twice, in each case with 5 ml of water. The combined aqueous phases are filtered, then the water is evaporated in a vacuum. The residue is purified by column chromatography on Sephadex G-25. Yield: 0.41 g (52%); brown powder.

Variant B. 2.84 g (5 mmol) of TPPTS in 10 ml of water are stirred into a solution of 0.32 g (1 mmol) of dipotassium tetrachloropalladate(II), K$_2$[PdCl$_4$], in 10 ml of water at 25° C., the reaction solution turning brown. Then 170 mg (4.5 mmol) of sodium tetrahydridoborate, Na[BH$_4$], in 5 ml of water are added dropwise over a period of 30 minutes. Stirring is continued for another 90 minutes and then the water is removed in a vacuum. The residue is washed twice, in each case with 5 ml of ethanol, and then purified by column chromatography on Sephadex G-25. Yield: 1.62 g (82%); brown powder.

Characterization: $^{31}$P-NMR (109.3 MHz, D$_2$O, 5° C.: $\delta=22.6$ ppm (s). IR (cm$^{-1}$, KBr): $\nu$(SO)=1225 (sh, vst), 1200 (vst), 1039 (vst), 622 (vst).

Element analysis (C$_{54}$H$_{54}$Na$_9$O$_{36}$P$_3$PdS$_9$; 1973.77): Calc. C 32.86; H 2.76; O 29.18; P 4.71; Pd 5.39; S 14.62 Found C 32.35; H 2.70; O 29.95; P 4.87; Pd 5.30; S 15.27.

Example 27: Synthesis of Pt(TPPTS)$_4$·12 H$_2$O

Variant A. 0.78 g (0.7 mmol) of tetrakis(triphenylphosphane)platinum, Pt[P(C$_6$H$_5$)$_3$]$_4$, are dissolved in 80 ml of toluene. 3.18 g (5.6 mmol) of TPPTS in 30 ml of water are stirred into the solution, whereupon the organic phase quickly loses its colour. In order to complete the reaction, stirring is continued for another 15 minutes at room temperature. After separation of the phases, the organic phase is washed twice, in each case with 10 ml of water. The combined aqueous solutions are filtered, the water is removed in a vacuum. The substance is purified by column chromatography on Sephadex G-25. Yield: 750 mg (40%); yellowish orange crystals.

Variant B. A solution of 2.84 g (5 mmol) of TPPTS in a mixture of 10 ml of water and 20 ml. of ethanol is heated to 70° C. After 80 mg (2 mmol) of sodium hydroxide have been added, a total of 0.42 g (1 mmol) of dipotassiumtetrachloroplatinate(II), $K_2[PtCl_4]$, in 5 ml of water are added dropwise over a period of 1 hour. The solution turns orange-yellow. Stirring is continued for another 2 hours and the solvent is removed in a vacuum. The residue is purified by column chromatography on Sephadex G-25. Yield: 1.21 g (45%); yellowish-orange crystals.

Variant C. 200 mg (0.24 mmol) of the peroxo-complex $Pt(\eta^2-O_2)[P(C_6H_5)_3]_2 \cdot C_6H_6$ are dissolved in 10 ml of methylene chloride. 1.71 g (3 mmol) of TPPTS in 10 ml of water are added and the resultant two-phase system is stirred for 5 hours at 25° C. After separation of the phases the organic phase is washed with 10 ml of water. The combined aqueous phases are washed with 10 ml of methylene chloride, then the water is removed in a vacuum and the raw product is purified by column chromatography on Sephadex G-25. Yield: 240 mg (37%); yellow crystals.

Characterization: $^{31}$P-NMR (109.3 MHz, $D_2O$, 5° C.): $\delta = 22.2$ ppm (d) [$^1J(Pt,P) = 2853$ Hz, $3J(P,P) = 19.8$ Hz; $\delta = 24.1$ ppm (m) [$^1J(Pt-P) = 2210$ Hz]. IR (KBr, cm$^{-1}$) $\nu(SO) = 1226$ (sh, vst), 1201 (vst), 1039 (vst), 622 (vst).

Element analysis ($C_{72}H_{60}Na_{12}O_{48}P_4PtS_{12}$; 2684.94): Calc. C 32.21; H 2.70; O 28.60; P 4.61; Pt 7.27; S 14.33 Found C 32.21; H 2.58; O 27.62; P 4.61 Pt 7.03; S 14.86.

Example 28: Synthesis of $PtCl_2(TPPTS)_2 \cdot 6\ H_2O$

A solution of 0.21 g (0.5 mmol) of dipotassium-tetrachloroplatinate(II), $K_2[PtCl_4]$, in 5 ml of water is added dropwise at 25° C. to 0.57 g (1 mmol) of TPPTS in 10 ml of water slowly enough to ensure that the colour is always lost. Then the mixture is stirred for 20 hours and the water is removed in a vacuum. The product still contains residual potassium chloride which cannot be separated by means of gel chromatography as the platinum complex quickly decomposes on conventional support materials. Yield: 0.69 g (91%); yellowish powder.

Characterization: $^{31}$P-NMR (109.3 MHz, $D_2O$, 5° C.): $\delta = 13.9$ ppm [$^1J(Pt,P) = 3727$ Hz]; IR (cm$^{-1}$, KBr): $\nu(SO) = 1226$ (sh, vst), 1201 (vst), 1039 (vst), 623 (vst); $\nu(Pt-Cl) = 313$ (w)

Example 29: Synthesis of $Cu_3(TPPTS)_2[\mu-P(C_6H_4-m-SO_3Na)_2(C_6H_4-m-SO_3)]_3 \cdot 12\ H_2O$ A solution of 282.5 mg of TPPTS and 62.4 mg of $CuSO_4 \cdot 5\ H_2O$ in 10 ml of distilled water is stirred for 2 hours at room temperature. The originally light-blue solution first turns green and is yellow after the reaction has been completed. The solution is concentrated in a vacuum to ⅓ of its original volume and then covered with the same amount of ethanol. After it has been allowed to stand for 3 days at room temperature, white crystals precipitate. They are separated, dissolved in 5 ml of distilled water and then subjected to column chromatography on Sephadex G-25 (column: diameter 2.4 cm, length 1.20 m). The first fraction is collected. When the eluate is concentrated in a vacuum, white crystals are obtained which soon turn brick-red when left to stand in the air. The yield is 397 mg (40%).

Characterization: $^{31}$P-NMR (109.3 MHz, $D_2O$, 28° C.): $\delta = -2.93$ ppm.

Element analysis ($C_{90}H_{84}Cu_3O_{57}Na_{12}P_5S_{15}$; 3177.62) Calc. C 33.90; H 2.84; Cu 5.90; P 4.80; Found C 31.99; H 2.97; Cu 5.0; P 3.95.

Example 30: Synthesis of $Ag(TPPTS)_2[P(C_6H_4SO_3Na)_2(C_6H_4-m-SO_3)] \cdot 8\ H_2O$ Variant A: 1.14 g (2 mmol) of TPPTS in 10 ml of water are added to 68 mg (0.4 mmol) of silver nitrate in 5 ml of water and stirred for 7 hours at room temperature, during which time the silver nitrate dissolves completely. The water is removed from the clear solution in an oil-pump vacuum. The glassy residue is purified by column chromatography on Sephadex G-15. Yield: 710 mg (92%); colourless, slightly light-sensitive powder.

Variant B: 1.14 g (2 mmol) of TPPTS in 15 ml of water are added to 70 mg (0.5 mmol) of silver chloride and stirred for 2 days at room temperature. Afterwards the silver chloride has dissolved, forming the complex compound. The water is removed from the clear solution in an oil-pump vacuum. The glassy residue is purified by column chromatography on Sephadex G-15. Yield: 860 mg (89%); colourless, slightly light-sensitive powder.

Characterization: $^{31}$P-NMR (109.3 MHz, $D_2O/C_2H_5OH$, $-30°$ C.): $\delta = 8.9$ ppm (dd), [$^1J(^{107}Ag,P) = 314$ Hz; $^1J(^{109}Ag,P) = 358$ Hz]IR (KBr, cm$^{-1}$) $\nu(SO) = 1224$ (sh, vst), 1198 (vst), 1040 (vst), 622 (vst).

Element analysis ($C_{54}H_{52}AgNa_8O_{35}P_3S_9$; 1934.23): Calc. C 33.53; H 2.71; Ag 5.58; O 28.95; P 4.80; S 14.92; Found C 33.15; H 2.76; Ag 5.70; O 28.98; P 4.79; S 14.89.

Example 31: Synthesis of $Au_2(TPPTS)_2[\mu-P(C_6H_4-m-SO_3Na)_2(C_6H_4-m-SO_3)]_2 \cdot 8H_2O$ 150 mg (0.44 mmol) of tetrachlorogold(III) acid are dissolved in 5 ml of water saturated with nitrogen. A few seconds after the addition of 500 mg (0.88 mmol) of TPPTS the solution begins to lose colour. After 2–3 minutes it is colourless. After 4 hours of stirring, the water is removed in a vacuum and the residue dried in a vacuum (0.01 Torr corresponding to 1.33 Pa) Yield: 382 mg (31%); colourless brittle glass.

Characterization: $^{31}$P-NMR (109.3 MHz, $D_2O$, 5° C.): $\delta = 43.23$ ppm (broad signal).

Element analysis ($C_{72}H_{68}Au_2Na_{10}P_4O_{46}S_{12}$; 2801.7): Calc. C 30.87; H 2.45; Au 14.06; P 4.42; S 13.73; Found C 30.40; H 3.00; Au 12.90; P 3.06; S 11.90.

Example 32: Synthesis of $Au_2(TPPTS)_4[\mu-P(C_6H_4-m-SO_3Na)_2(C_6H_4-m-SO_3)]_2 \cdot 16\ H_2O$ 0.52 g (2 mmol) of carbonyl chlorogold, (CO)AuCl, are dissolved in 20 ml of toluene. As soon as 3.52 g (6 mmol) of TPPTS in 10 ml of water are added, a flaky white precipitate is formed. Stirring is performed for 15 hours at room temperature, during which the precipitate dissolves. After the phases have separated, the organic phase is washed twice, in each case with 5 ml of water. The combined aqueous phases are filtered and evaporated in a vacuum until dry. The raw product is purified by column chromatography on Fractogel TSK HW-40 or Sephadex G-15. Yield: 1.08 g (54%, related to TPPTS); pale-yellow powder.

Characterization: $^{31}$P-NRM (109.3 MHz, D$_2$O, 5° C.): $\delta = 41.7$ ppm (s). IR (KBr, cm$^{-1}$) v(SO) = 1226 (sh, vst), 1201 (vst), 1041 (vst), 623 (vst).

Element analysis (C$_{108}$H$_{104}$Au$_2$Na$_{16}$O$_{70}$P$_6$S$_{18}$; 4046.66): Calc. C 32.06; H 2.59; Au 9.73; Cl 0.0; O 27.68; P 4.59; S 14.26; Found C 30.96; H 2.46; Au 10.40; Cl 0.0; O 26.40; P 4.14; S 14.87.

Example 33: Synthesis of Au$_2$S(TPPTS)$_2$·6 H$_2$O

Variant A. 90 mg (0.28 mmol) of chloro(tetrahydrothiophene)gold(I) are dissolved in methylene chloride. A solution of 120 mg (0.28 mmol) of TPPTS in 10 ml of water is added to this solution to form a lower layer and the two-phase system is stirred intensively for 15 hours. Then the water phase is separated and evaporated in a vacuum until dry. Yield: 70 mg (15%).

Variant B. A solution of 200 mg (0.07 mmol) of the compound from example 31 in 3 ml of ethanol-water (3+1 parts by volume) is cooled to 0° C. On addition of 0.5 ml of a sodium sulfide solution saturated with nitrogen (7.5%; 0.12 mmol) a white milkiness occurs, which disappears again on addition of approx. 1 ml of water. The solvent is removed and the residue is dried in an oil-pump vacuum. Yield: 39 mg (33%); yellow powder, which turns brown when it is stored for longer periods at room temperature (formation of gold sulfide). The product is purified by column chromatography on Sephadex G-25 under the exclusion of light.

Characterization: $^{31}$P-NMR (109.3 MHz, D$_2$O, 5° C.): $\delta = 31.76$ ppm.

Element analysis (C$_{36}$H$_{36}$Au$_2$Na$_6$O$_{24}$P$_2$S$_7$; 1670.5): Calc. C 25.80; H 2.10; Au 23.50; P 3.70; S 13.40; Found C 24.30; H 2.20 Au 23.00 P 3.00; S 12.90.

The following examples 34 to 56 describe the use of the new compounds as catalysts.

Example 34: Catalytic hydrogenation of cyclohexene in the presence of Co$_2$(CO)$_6$(TPPTS)$_2$·6 H$_2$O as a catalyst 31 mg (0.02 mmol) of Co$_2$(CO)$_6$(TPPTS)$_2$·6 H$_2$O, dissolved in 2 ml of water, as well as 820 mg (10 mmol) of freshly distilled cyclohexene are placed in a 100 ml laboratory autoclave under an argon atmosphere. The mixture is left to react for 20 hours at a hydrogen pressure of 3.0 MPa and 20° C. and then the phases are separated. According to a GC/MS analysis the organic phase consists of 7% cyclohexane and 93% cyclohexene.

Example 35: Selective hydrogenation of 1-decene under hydroformylation conditions in the presence of Co$_2$(CO)$_6$(TPPTS)$_2$·6 H$_2$O as a catalyst A solution of 31 mg (0.02 mmol) of Co$_2$(CO)$_6$(TPPTS)$_2$·6 H$_2$O in 2 ml of water and 0.70 g (5 mmol) of 1-decene is placed in a 50 ml laboratory autoclave which has been rinsed for 15 mins with nitrogen. Then the mixture is left to react for 16 hours at 100° C. and a pressure of 7.0 MPa H$_2$/CO (1:1). After cooling to 25° C. the organic phase is extracted with 2 ml of methylene chloride. The GC/MS analysis shows 76% ndecane and 24% unchanged 1-decene. A corresponding aldehyde cannot be detected.

Example 36: Catalytic hydrogenation of cyclohexene and cis-cyclooctene in the presence of Rh(NO)(TPPTS)$_3$·9 H$_2$O as a catalyst a) Hydrogenation of cyclohexene without a solvent: 20 mg of Rh(NO)(TPPTS)$_3$·9 H$_2$O(0.01 mmol) in 1.5 ml of distilled water are placed in hydrogenation apparatus to Marhan. 330 mg (4 mmol) of cyclohexene are added to this solution, the apparatus is rinsed with H$_2$ and left to react at 25° C. and 0.1 MPa H$_2$ pressure for 92 hours. The organic phase is taken up with 3 ml of methylene chloride and dried over water-free sodium sulfate According to GC/MS analysis the product consists of 63.3% cyclohexane and 36.7% cyclohexene.

b) Hydrogenation of cyclohexene in solution: 40 mg (0.02 mmol) of Rh(NO)(TPPTS)$_3$·9 H$_2$O in a mixture of 3 ml of water and 3 ml of isopropanol are placed in hydrogenation apparatus to Marhan. 410 mg (5 mmol) of cyclohexene are added to this solution, the apparatus is rinsed briefly with H$_2$ and left to react at 25° C. and 0.1 MPa H$_2$ pressure for 120 hours. The organic phase is taken up with 3 ml of methylene chloride and dried over water-free Na$_2$SO$_4$. According to GC/MS analysis the product consists of 47% cyclohexane and 53% cyclohexene.

c) Hydrogenation of cyclooctene under normal pressure: 100 g (0.05 mmol) of Rh(NO)(TPPTS)$_3$·9 H$_2$O in 5 ml of water are placed in hydrogenation apparatus to Marhan under an H$_2$ atmosphere (0.1 MPa). Then 2.20 g (20 mmol) of freshly distilled cis-cyclooctene are added and the resultant two-phase mixture is stirred for 43 hours at 25° C. The GC/MS analysis of the organic phase shows a cyclooctane/cyclooctene ratio of 30:70. After the experiment has run for 150 hours the cyclooctane/cyclooctene ratio is 98:2.

Example 37: Catalytic hydrogenation of cis-cyclooctene with IrCl($\eta$-1,5-C$_8$H$_{12}$)(TPPTS)$_2$·6 H$_2$O as a catalyst 2.75 g (25 mmol) of cis-cyclooctene and 79 mg (0.05 mmol) of ($\eta^4$-1,5-C$_8$H$_{12}$)IrCl(TPPTS)$_2$·6 H$_2$O in 3 ml of water are placed in a 50 ml laboratory autoclave. After the autoclave has been rinsed twice with hydrogen, H$_2$ is injected until a pressure of 2.5 MPa is reached, then the mixture is heated for 20 hours to 100° C. The pressure rises to 3 MPa. After cooling to room temperature, the phases are separated. The GC/MS analysis of the organic phase shows that 64% cyclooctane and 36% cis-cyclooctene are present in the reaction product.

Example 38: Catalytic reduction of nitrobenzene with carbon monoxide in the presence of Fe-TPPTS complex compounds as catalysts a) 470 mg (1.29 mmol) of Fe$_2$(CO)$_9$ are boiled with a solution of 587 mg (1.29 mmol) of TPPTS in 50 ml of water for t$_1$ [min]. Then 10 ml of nitrobenzene with 3 ml of ethanol are added and the mixture is boiled for another t$_2$ min) (cf. table 1) with reflux and CO-feed (0.1 MPa). After cooling the phases are separated. The nitrobenzene phase is freed from finely distributed iron hydroxide by passing it through a dense filter and then shaken with 1% hydrochloric acid. This extract is evaporated and the yield of aniline is determined. In addition, before shaking with 1% hydrochloric acid a sample of the nitrobenzene is taken for GC/MS analysis. The results are compiled in table 1.

The red complex Fe$_4$(CO)$_{11}$(TPPTS) can be isolated from these preparations as a catalytically active compound and is then purified by gel chromatography on Sephadex G-15. For this purpose the following procedure is adopted:

The aqueous filtrate is concentrated to 30 ml in a vacuum. In order to isolate the catalytically active complex, 40 g of Sephadex G-15 in a 25-30 cm thick layer are applied to a glass sinter which is roughly 4 cm in diameter. The filtrate is added in the fast stream and two yellow fractions are extracted; they contain the complexes $Fe(CO)_4(TPPTS)$ and $Fe(CO)_3$-$(TPPTS)_2$ (cf. example 2). Then a brown zone is eluted at a flow rate of 1 drop/sec with pure water until the last remaining deep-red, extremely slow-moving zone has reached the end of the column. A red, intensively colored complex is extracted with water/ethanol (ratio 3:1, total 50 ml; then ratio 1:1) until the gel is only slightly pink in colour. At least 750 ml of eluent are required. After the solvent has been removed in a vacuum, 110 mg of the new complex remain (2 wt. %, related to the $Fe_2(CO)_9$ used).

Characterization: $^{31}$P-NMR (109.3 MHz, $D_2O+5°$ C.): $\delta = 84.81$ ppm. IR [KBr, cm$^{-1}$] 2052 m, 2002 w, sh, 1963 w, 1900-1835 (numerous shoulders).

Element analysis ($C_{29}H_{18}Fe_4Na_3O_{23}PS_3$; 1153.92): Calc. C 30.19; H 1.57; Fe 19.36; P 2.68; Found C 30.00; H 1.40; Fe 19.00; P 2.40.

TABLE 1

| | | | Hydrogenation of nitrobenzene | |
|---|---|---|---|---|
| $t_1$ (min) | $t_2$ (min) | Pressure (MPa) | Molar ratio* (GC/MS-determination) | Aniline HCl (mg) |
| 15 | 120 | 0.1 | 1/134 (=0.75%) | 89 |
| 20 | 120 | 0.1 | 1/100 (=1%) | 120 |
| 30 | 120 | 0.1 | 1/108 (=0.93%) | 112 |
| 60 | 120 | 0.1 | 1/23 (=4.4%) | 380 |

*Aniline/Nitrobenzene b) 45 mg (0.13 mmol) of Fe (CO)$_{12}$ are boiled for 1 hour with 175 mg (0.28 mmol) of TPPTS in 7 ml of water and 3 ml of ethanol with reflux, a black powder precipitating. The yellow filtered solution is mixed with 3 ml of 10% KOH and 10 ml of nitrobenzene. Whilst CO is fed in, the mixture is boiled for another 2 hours with reflux. After phase separation the nitrobenzene phase is treated as described under a).

Analysis: GC/MS, aniline/nitrobenzene 1/20; thin layer chromatogram/(silica gel plate), toluene/methanol 10/1 as solvent, plate not saturated): $R_f=0.49$ [aniline], $R_f=0.87$ [nitrobenzene], $R_f=0.30$ [unknown].

Example 39: Catalytic reduction of nitrobenzene with CO in the presence of $Co_2(CO)_6(TPPTS)_2$·6 $H_2O$ as a catalyst 62 mg (0.04 mmol) of $Co_2(CO)_6(TPPTS)_2$·6 $H_2O$ in 5 ml of water and 490 mg (4 mmol) of nitrobenzene are placed in a 100 ml laboratory autoclave, which has previously been rinsed for 15 min with nitrogen.

(a) The mixture is stirred for 12 hours at 100° C. and 4.0 MPa CO pressure and the organic phase is then extracted with 5 ml of methylene chloride. The GC/MS analysis shows 4% aniline and 96% nitrobenzene.

(b) The same procedure is adopted as in (a), but the mixture is stirred for 40 hours at 140° C. and 2.5 MPa CO pressure. Result (GC/MS analysis): 16.4% aniline, 83.6% nitrobenzene.

(c) The same procedure is adopted as in (a), but the mixture is stirred for 40 hours at 140° C. and 5.5 MPa CO pressure. Result (GC/MS analysis): 38.4% aniline, 61.6% nitrobenzene.

Example 40: Hydrocarbonylation of ethylene with $Co_2(CO)_6(TPPTS)_2$·6 $H_2O$ as a catalyst 153 mg (0.1 mmol) of $Co_2(CO)_6(TPPTS)_2$·6 $H_2O$ in 5 ml of water are placed in a 50 ml laboratory autoclave under a nitrogen atmosphere. Then ethylene is injected up to a pressure of 0.5 MPa (approx. 10 mmol) and CO up to a pressure of 4 MPa. The mixture is heated to 145° C. and left to react for 40 hours at this temperature. After cooling to room temperature 2 ml of methylene chloride are added and the organic phase is examined using GC/MS analysis; apart from methylene chloride only diethylketone [$v(CO) = 1729$ cm$^{-1}$] can still be detected. The conversion is approx. 10%.

Example 41: Hydroformylation of 1-hexene in the presence of $Co_2(CO)_6(TPPTS)_2$·6 $H_2O$ as a catalyst 1.) 62 mg (0.04 mmol) of $Co_2(CO)_6(TPPTS)_2$·6 $H_2O$ and 0.45 g (0.08 mmol) of TPPTS in 3 ml of water are placed in a 50 ml laboratory autoclave under a nitrogen atmosphere. 1.62 g (20 mmol) of 1-hexene are added and $CO/H_2$ is injected up to a pressure of 7 MPa. The mixture is heated to 110° C. and left to react for 18 hours at this temperature. After cooling to room temperature, the phases are separated. The GC/MS analysis of the organic phase shows that the conversion of 1-hexene to heptanal(1) is 36%, with an n/i ratio of 3.4:1.

2.) The aqueous phase is again mixed with 1.62 g (20 mmol) of 1-hexene. Hydroformylation is repeated under the same conditions as in 1. The GC/MS analysis of the organic phase shows that the conversion of 1-hexene to heptanal(1) is 35%, with an n/i ratio of 2.1:1.

3.) 153 mg (0.01 mmol) of $Co_2(CO)_6(TPPTS)_2$·6 $H_2O$ in 5 ml of water are placed in a 50 ml laboratory autoclave under a nitrogen atmosphere. 0.84 g (1 mmol) of 1-hexene are added and CO injected to a pressure of 5.5 MPa. The two-phase mixture is heated to 170° C. After 20 hours of reaction at this temperature, it is left to cool to room temperature and the phases are separated. The GC/MS analysis of the organic phase shows that the 1-hexene has been completely reacted to heptanal(1) with an n/i ratio of 1:1.

Example 42: Hydroformylation of ethylene with $RhCl(CO)(TPPTS)_2$·6 $H_2O$ as a catalyst under a CO atmosphere 141 mg (0.1 mmol) of $RhCl(CO)(TPPTS)_2$·6 $H_2O$ dissolved in 3 ml of water are placed in a 50 ml laboratory autoclave under a nitrogen atmosphere. Then ethylene is injected up to a pressure of 0.5 MPa (approx. 10 mmol) and then CO up to a pressure of 3 MPa. The mixture is heated to 120° C. and left to react for 22 hours at this temperature. After cooling to 0° C. the organic phase is isolated. The GC/MS and GC/IR analyses show that 0.65 g (approx 20%) of propanal [$v(CO)=1743$ cm$^{-1}$] have formed.

Example 43: Hydroformylation of 1-hexene with $RhCl(CO)(TPPTS)_2$·6 $H_2O$ as a catalyst under a CO atmosphere 70 mg (0.05 mmol) of $RhCl(CO)(TPPTS)_2$·6 $H_2O$ in 3 ml of water are placed in a 50 ml laboratory autoclave under a nitrogen atmosphere. Then 0.84 g (10 mmol) of 1-hexene are added and CO injected up to a pressure of 4 MPa. The two-phase mixture is heated to 100° C.

After 18 hours of reaction at this temperature, it is left to cool to room temperature and the organic phase is isolated. The GC/MS analysis shows that the conversion of 1-hexene to heptanal(1) is 92% with an n/i-ratio of 76–24.

Example 44: Hydroformylation of 1-hexene in the presence of $Rh_6(CO)_7(TPPTS)_9 \cdot 27\ H_2O$ as a catalyst 65 mg (0.01 mmol) of $Rh_6(CO)_7(TPPTS)_9 \cdot 27\ H_2O$ and 0.17 g (0.3 mmol) of TPPTS in 3 ml of water are placed in a 100 ml laboratory autoclave under a nitrogen atmosphere. After addition of 1.62 g (20 mmol) of 1-hexene, $CO/H_2$ is injected up to a pressure of 5 MPa and the two-phase system is heated with vigorous stirring for 18 hours to 105° C., the pressure rising to 5.7 MPa. After the reaction has been completed, the phases are separated. The organic phase is examined using GC/MS analysis. The aqueous phase containing the catalyst is reused for hydroformylation of the same amount of 1-hexene under the above-mentioned conditions.

a) The GC/MS analysis of the colourless organic phase shows 84% conversion of 1-hexene to heptanal(1) with an n/i ratio of 95:5.

b) The GC/MS analysis of the organic phase shows 78% conversion of 1-hexene to heptanal(1) with an n/i-ratio of 94:6.

c) The GC/MS analysis of the organic phase shows 75% conversion of 1-hexene to heptanal(1) with an n/i ratio of 90:10.

d) The GC/MS analysis of the organic phase shows 74% conversion of 1-hexene to heptanal(1) with an n/i ratio of 84:16.

Example 45: Hydroformylation of 1-hexene in the presence of $IrH(CO)(TPPTS)_3 \cdot 9\ H_2O$ as a catalyst 63 mg (0.03 mmol) of $IrH(CO)(TPPTS)_3 \cdot 9\ H_2O$ and 0.51 g (0.9 mmol) of TPPTS in 3 ml of water are placed in a 50 ml laboratory autoclave under a nitrogen atmosphere. After the addition of 2.52 g (30 mmol) of 1-hexene, $CO/H_2$ is injected up to a pressure of 5 MPa and the two-phase system is heated to 110° C., the pressure rising to 6.5 MPa. After 20 hours of reaction at this temperature, it is left to cool to room temperature and the phases are separated. The GC/MS analysis of the organic phase shows that the conversion of 1-hexene to heptanal(1) is 15%, with an n/i ratio of 93:7.

Example 46: Hydroformylation of 1-hexene in the presence of $(cis\text{-}C_{12})Pt(TPPTS)_2 \cdot 6\ H_2O$ as a catalyst 45 mg (0.03 mmol) of $cis\text{-}C_{12}Pt(TPPTS)_2 \cdot 6\ H_2O$ in 2 ml of water are placed in a 50 ml laboratory autoclave under an $N_2$ atmosphere. After the addition of 2.43 g (30 mmol) of 1-hexene, $CO/H_2$ is injected at room temperature to a pressure of 7 MPa and the two-phase system is left to react for 18 hours at 100° C., the pressure rising to 8 MPa. After the reaction has been completed, the reaction solution is left to cool to room temperature and the phases are separated. The GC/MS analysis of the colourless organic phase shows that 58% of the 1-hexene has been hydroformylated Lo heptanal(1), with an n/i ratio of 2:1. The aqueous phase is again mixed with 2.43 g (30 mmol) of 1-hexene. The hydroformylation is performed under the same conditions; 62% heptanal(1) (n/i ratio 2.2:1) is obtained.

Example 47: Hydroformylation of 1-hexene in the presence of $(cis\text{-}C_{12})Pt(TPPTS)_2 \cdot 6\ H_2O/SnCl_2$ as a catalyst A 50 ml laboratory autoclave is charged, with 45 mg (0.03 mmol) of $cis\text{-}Cl_2Pt(TPPTS)_2 \cdot 6\ H_2O$ and 7 mg (0.03 mmol) of $SnCl_2 \cdot 2\ H_2O$ in 2 ml of water. After addition of 2.43 g (30 mmol) of 1-hexene, $CO/H_2$ is injected up to a pressure of 7 MPa. The mixture is heated to 100° C., the pressure rising to 8 MPa, and stirred for 18 hours at this temperature. After cooling to room temperature the phases are separated. The GC/MS analysis of the colourless organic phase shows that 1-hexene has been completely reacted to a mixture of 70 wt. % n-heptanal(1), 26 wt. % i-heptanal(1) and 4 wt. % n-heptanol(1).

Example 48: Catalytic oxidation of cyclohexene with iodosylbenzene and $RuCl_2(TPPTS)_2 \cdot 6\ H_2O$ as a catalyst 82 mg (1 mmol) of cyclohexene and 30 mg (0.02 mmol) of $RuCl_2(TPPTS)_2 \cdot 6\ H_2O$ in 2 ml of water are added to a suspension of 0.33 g (1.5 mmol) of iodosylbenzene in 5 ml of methylene chloride and stirred for 5 hours between 10° C. and 15° C. The GC/MS and GC/IR analyses of the organic phase show that 70% of the cyclohexene is oxidised to cyclohexene oxide.

Example 49: Catalytic oxidation of cyclohexanol with $RuCl_2(TPPTS)_2 \cdot 6\ H_2O$ as a catalyst 100 mg (1 mmol) of cyclohexanol and 30 mg (0.02 mmol) of $RuCl_2(TPPTS)_2 \cdot 6\ H_2O$ in 2 ml of water are added to a suspension of 0.33 mg (1.5 mmol) of iodosylbenzene in 5 ml of methylene chloride. The mixture is left to react for 3 hours at room temperature and the organic phase is isolated. The GC/MS analysis shows that cyclohexanol is completely oxidised to cyclohexanone.

Example 50: Catalytic oxidation of 1-phenylethanol(1) with iodosylbenzene and $Pd(TPPTS)_3 \cdot 9\ H_2O$ as a catalyst 49 mg (4 mmol) of 1-phenylethanol(1) and 80 mg (0.04 mmol) of $Pd(TPPTS)_3 \cdot 9\ H_2O$ in 3 ml of water are added to a suspension of 1.32 g (6 mmol) of iodosylbenzene in 5 ml of methylene chloride and stirred for 15 hours at room temperature. The GC/MS analysis of the organic phase shows that 35% of the 1-phenylethanol(1) is oxidised to acetophenone.

Example 51: Catalytic oxidation of triphenylphosphane with $Pd(TPPTS)_3 \cdot 9\ H_2O$ as a catalyst 1) 60 mg (0.03 mmol) of $Pd(TPPTS)_3 \cdot 9\ H_2O$ in 4 ml of water are added to 2.62 g (10 mmol) of triphenylphosphane in 15 ml of toluene and the resultant two-phase mixture is vigorously stirred for 90 minutes in the air at room temperature. Then the organic phase is isolated by phase separation and dried over anhydrous sodium sulfate. The solvent is removed in a water-pump vacuum. The $^{31}P$-NMR spectrum shows that 86% of the phosphane is oxidised to triphenylphosphane oxide.

2) 60 mg (0.03 mmol) of $Pd(TPPTS)_3 \cdot 9\ H_2O$ in 4 ml of water are added to a solution of 2.62 g (10 mmol) of triphenylphosphane in 15 ml of toluene at room temperature and oxygen is passed through the resultant two-phase mixture for 90 minutes. The organic phase is isolated by phase separation and dried over anhydrous sodium sulfate. After the solvent has been removed, the residue is crystallised out of toluene. Yield: 2.77 g (99%) O=P(C$_6$H$_5$)$_3$; colourless crystals.

Characterization: $^{31}$P-NMR (109.3 MHz, C$_7$D$_8$, 20° C.): δ=26.3 ppm (s) IR (KBr, cm$^{-1}$) v(P=O)=1187 (vst), 1117 (vst).

Example 55: Catalytic carbon-carbon linking the presence of Pd(TPPTS)$_3$/CuI as a catalyst a) 40 mg (0.20 mmol) of copper(I)-iodide are stirred into a mixture of 10 ml of diethylamine, 1.78 g (11 mmol) of 3-ethyl-3-methyl-1-bromoallene, 1.02 g (10 mmol) of phenylacetylene and 200 mg (0.1 mmol) of Pd(TPPTS)$_3$·9 H$_2$O. After 15 hours of stirring at room temperature 3 ml of water are added and the diethylamine is removed in an oil-pump vacuum. The residue is extracted three times, in each case with 30 ml of n-pentane and then washed three times, in each case with 30 ml of a saturated aqueous sodium chloride solution. After drying over anhydrous sodium sulfate the solvent is removed in a vacuum. The product 2-ethyl-6-phenyl-hexadiene(2.3)-ine(5), CH$_3$C(C$_2$H$_5$)C=C=C(H)C≡C(C$_6$H$_5$), is purified by chromatography on silica gel (0.063–0.200 mm) petroleum ether-diethylether (50:1) or by distillation in a rotating bulb tube. Yield: 1.10 g (60%, related to phenylacetylene), yellow oil.

b) 30 mg (0.16 mmol) of copper(I)-iodide are stirred into a mixture of 200 mg of NaOH 45 mmol) in 10 ml of water, 680 mg (4.2 mmol) of 3-ethyl-3-methyl-1-bromoallene, 400 mg (4.0 mmol) of phenylacetylene and 160 mg (0.08 mmol) of Pd(TPPTS)$_3$·9 H$_2$O. The mixture is stirred for 40 hours at room temperature and then extracted three times, in each case with 25 ml of n-pentane. The organic phase is washed three times, in each case with 20 ml of saturated sodium chloride solution and dried over anhydrous sodium sulfate; then the solvent is removed in a vacuum. Yield after purification: 100 mg (14%, related to phenylacetylene).

Characterization: $^1$H-NMR (270 MHz, 25° C., CDCl$_3$): δ=1.03 ppm (t, 3 H, $^3$J=7.5 Hz) CH$_2$CH$_3$, δ=1.75 ppm (d, 3 H, $^5$J=2.9 Hz)=C(CH$_3$), δ=1.97–2.14 ppm (m, 2H) CH$_2$CH$_3$, δ=5.52 (sext. 1 H, $^5$J=2.8 Hz)=C(H), δ=7.22–7.42 ppm (m, 5H) C$_6$H$_5$ IR (Film, cm$^1$) v(C≡C)=2207; v(C=C=C)=1947 c) 30 mg (0.16 mmol) of copper(I)iodide are stirred into a mixture of 0.2 g (5 mmol) of sodium hydroxide and 0.16 g (0.08 mmol) of Pd(TPPTS)$_3$·9 H$_2$O in 10 ml of water. Then 0.68 g (4.2 mmol) of 3-ethyl-3-methyl-1-bromoallene and 0.4 g (4 mmol) of phenylacetylene in 10 ml of pentane are added. The mixture is stirred for 20 hours at room temperature and the phases are separated. The aqueous phase is extracted twice, in each case with 15 ml of pentane. The organic phase is washed three times, in each case with 20 ml of sodium chloride solution and dried over anhydrous sodium sulfate. Then the solvent is removed in a vacuum. Yield after purification: 0.25 g (35%, related to phenylacetylene); yellow oil Characterization: $^1$H-NMR (270 MHz, 25° C., CDCl$_3$): δ=1,03 ppm (t, $^3$H, 3J=7,5 Hz) CH$_2$CH$_3$, δ=1,75 ppm (D, 3H, $^5$J=2,9 Hz)=C(CH$_3$), δ=1,97–2,14 ppm (m, 2H) CH$_2$CH$_3$, δ=5,52 (sext. 1H, $^5$J=2,8 Hz)=C(H), δ=7,22–7,42 ppm (m, 5H) C$_6$H$_5$ IR (Film. cm$^{-1}$) v(C≡C)=2207, v(C=C=C)=1947

Example 53: Amine addition to a carbon-carbon double bond

A solution of 60 mg (0.04 mmol) of PtCl$_2$(TPPTS)$_2$·6 H$_2$O in 3 ml of water, 4.08 g (60 mmol) of isoprene and 2.93 g (40 mmol) of diethylamine are placed in a 50 ml laboratory autoclave, which has been rinsed for 15 minutes with nitrogen. Then the mixture is heated for 2 days to 80° C., a pressure of 0.2–0.3 MPa is reached. After cooling to room temperature the phases are separated and the organic phase is dried over anhydrous sodium sulfate. The GC/MS analysis shows 1-(N,N-diethylamino)-3-methylbutene(2), (CH$_3$)$_2$C=CHCH$_2$N(C$_2$H$_5$)$_2$ in 69% yield [v(C=CH)=1670 cm$^{-1}$; δ(=CH==843 cm$^{-1}$]. Furthermore 22% 1-(N,N-diethylamino)-2-methylbutene(2), CH$_3$CH=C(CH$_3$)—CH$_2$N(C$_2$H$_5$)$_2$, in 22% yield [v(C=CH)=1653 cm$^{-1}$; δ(=CH)=823 cm$^{-1}$] is also formed.

We claim:

1. A complex compound comprising a central atom selected from the group consisting of elements of Groups IB, VIIA, and VIIIA of the IUPAC Periodic Table, said compound containing a trisodium salt of tris(m-sulfophenyl)-phosphine as a complex ligand, excluding a reaction product of bis(1,5cyclooctadiene)-nickel with said salt, said compound being of the formula

$$L_w^1 L_x^2 M_y[P(C_6H_4\text{—m-SO}_3Na)_3]_z$$

wherein L$^1$ and L$^2$ are individually ligands which, in addition to said salt, are bound to said central atom, M is said central atom, w, x, y, and z are integers, w and x are 0 to 7y, y is 1 to 6, and z is ≦4y.

2. The compound of claim 1 comprising a further ligand taken from the class consisting of H, CO, NO, PF$_3$, H$_2$O, S, halogen, π-aromatic ligands, π-olefin ligands, and π-acetylene ligands.

3. The compound of claim 2 wherein said π-aromatic ligand is cyclopentadienyl.

4. The compound of claim 2 wherein said π-olefin ligand is cyclooctadiene.

5. The compound of claim 2 wherein said π-acetylene ligand is diphenylacetylene.

6. The compound of claim 1 wherein said central atom is manganese, iron, ruthenium, cobalt, rhodium, irridium, nickel, palladium, platinum, copper, silver, or gold.

7. The compound of claim 6 wherein said compound is taken from the class consisting of manganese compounds (η$^5$-C$_5$H$_5$)Mn(CO)$_2$P(C$_6$H$_4$—m-SO$_3$Na)$_3$], (η$^5$-C$_5$H )Mn(CO)P(C$_6$H$_4$—m-SO$_3$Na)$_3$]$_2$, iron compounds Fe(CO)$_4$[P(C$_5$H$_4$—m-SO$_3$Na)$_3$], Fe(CO)$_3$[P(C$_6$H$_4$—m-SO$_3$Na)$_3$]$_2$, Fe$_4$(CO)$_{11}$[P(C$_6$H$_4$—m-SO$_3$Na)$_3$], ruthenium compounds Ru(NO)$_2$[P(C$_6$H$_4$—m-SO$_3$Na)$_3$]$_2$, RuCl$_2$[P(C$_6$H$_4$—m-SO$_3$Na)$_3$]$_2$, cobalt compounds Co$_2$(CO)$_6$[P(C$_6$H$_4$—m-SO$_3$Na)$_3$]$_2$, CoH(CO)[P(C$_6$H$_4$—m-SO$_3$Na)$_3$]$_3$, CoH$_2$[P(C$_6$H$_4$—m-SO$_3$Na)$_3$]$_3$, Co$_2$(CO)$_4$(H$_5$C$_6$—C≡C—C$_6$C$_5$)[P(C$_6$H$_4$—m-SO$_3$Na)$_3$]$_2$, rhodium compounds RhCl[P(C$_6$H$_4$—m-SO$_3$Na)$_3$]$_3$, Rh(NO)[P(C$_6$H$_4$—m-SO$_3$Na)$_3$]$_3$, Rh(CH$_3$COO)[P(C$_6$H$_4$—m-SO$_3$Na)$_3$]$_3$, Rh(CO)(OH)[P(C$_5$H$_4$—m-SO$_3$Na)$_3$]$_2$, Rh(CO)Cl[P(C$_6$H$_4$—m-SO$_3$Na)$_3$]$_2$, Rh(μ-Cl)(CO)[P(C$_6$H$_4$—m-SO$_3$Na)$_3$]$_2$, Rh(OH)[P(C$_6$H$_4$—m-SO$_3$Na)$_3$]$_3$, Rh$_2$[P(C$_6$H$_4$—m-SO$_{m\text{-}SO3}$Na)$_3$]$_2$[P(C$_6$H$_4$—m-SO$_3$Na)$_2$(C$_6$H$_4$—m-SO$_3$)]$_2$, Rh$_2$(μ-Cl$_2$)(η$^4$-C$_8$H$_{12}$)[P(C$_6$H$_4$—m-SO$_3$Na)$_3$]$_2$, Rh$_6$(CO)$_7$P(C$_6$H$_4$—m-SO$_3$Na)$_3$]$_9$, iridium compounds Ir(NO)[P($C_6H_4$—m-$SO_3Na$)$_3$]$_3$, IrCl(CO)[P($C_6H_4$—m-$SO_3Na$)$_3$]$_3$, IrH(CO)P($C_6H_4$—m-$SO_3Na$)$_3$]$_3$, Ir($\mu$-Cl)($\eta^4$-$C_8H_{12}$)[P($C_6H_4$—m-$SO_3Na$)$_3$]$_2$, nickel compounds Ni[P($C_6H_4$—m-$SO_3Na$)$_3$]$_3$, Ni(CO)$_2$[P($C_6H_4$—m-$SO_3Na$)$_3$]$_2$, Ni(PF$_3$)$_2$[P($C_6H_4$—m-$SO_3Na$)$_3$]$_2$, a palladium compound Pd[P($C_6H_4$—m-$SO_3Na$)$_3$]$_3$, platinum compounds Pt[P($C_6H_4$—m-$SO_3Na$)$_3$]$_4$, PtCl$_2$[P($C_6H_4$—m-$SO_3Na$)$_3$]$_2$, a copper compound Cu$_3$[P($C_6H_4$—m-$SO_3Na$)$_3$]$_2$[$\mu$-P($C_6H_4$—m-$SO_3Na$)$_2$($C_6H_4$—m-$SO_3$)]$_3$, a silver compound Ag[P($C_6H_4$—m-$SO_3Na$)$_3$]$_2$[P($C_6H_4$—m-$SO_3Na$)$_2$($C_6H_4$—m-$SO_3$], and gold compounds Au$_2$[P($C_6H_4SO_3Na$)$_3$]$_2$[$\mu$-P($C_6H_4$—m-$SO_3Na$)$_2$-($C_6H_4$—m-$SO_3$)]$_2$, Au$_2$[P($C_6H_4$—m-$SO_3Na$)$_3$]$_4$[$\mu$-P($C_6H_4$—m-$SO_3Na$)$_2$($C_6H_4$—m-$SO_3$)]$_2$, Au$_2$S[P($C_6H_4$—m-$SO_3Na$)$_3$]$_2$.

* * * * *